United States Patent
Kirk et al.

(10) Patent No.: US 12,172,026 B2
(45) Date of Patent: *Dec. 24, 2024

(54) HIGH-POWER PULSED ELECTROMAGNETIC FIELD APPLICATOR SYSTEMS

(71) Applicant: Regenesis Biomedical, Inc., Scottsdale, AZ (US)

(72) Inventors: Martin L. Kirk, Scottsdale, AZ (US); John Y. Babico, Scottsdale, AZ (US); Frank E. Contreras, Phoenix, AZ (US); Joseph E. Bright, Phoenix, AZ (US); Donald B. Tate, Scottsdale, AZ (US)

(73) Assignee: Regenesis Biomedical, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/450,257

(22) Filed: Aug. 15, 2023

(65) Prior Publication Data

US 2024/0017085 A1    Jan. 18, 2024

Related U.S. Application Data

(63) Continuation of application No. 17/556,398, filed on Dec. 20, 2021, now Pat. No. 11,771,913, which is a continuation of application No. 17/040,636, filed as application No. PCT/US2019/023860 on Mar. 25, 2019, now Pat. No. 11,207,541.

(Continued)

(51) Int. Cl.
*A61N 2/02* (2006.01)
*G06K 7/10* (2006.01)

(52) U.S. Cl.
CPC .......... *A61N 2/02* (2013.01); *G06K 7/10366* (2013.01)

(58) Field of Classification Search
CPC .......... A61N 2/02; A61N 1/326; A61N 2/004; A61N 1/40; G06K 7/10366
See application file for complete search history.

(56) References Cited

U.S. PATENT DOCUMENTS

| | | |
|---|---|---|
| 4,926,881 A | 5/1990 | Ichinomiya et al. |
| 5,000,178 A | 5/1991 | Griffith |

(Continued)

FOREIGN PATENT DOCUMENTS

| | | |
|---|---|---|
| WO | WO2010/124234 A8 | 10/2010 |
| WO | WO2012/048302 A2 | 4/2012 |
| WO | WO2018/089773 A1 | 5/2018 |

OTHER PUBLICATIONS

Akan et al.; Extremely low-frequency electromagnetic fields affect the immune response of monocyte-derived macrophages to pathogens; Bioelectromagnetics; 31(8); pp. 603-612; Dec. 2010.

(Continued)

*Primary Examiner* — Akm Zakaria
(74) *Attorney, Agent, or Firm* — Shay Glenn LLP

(57) ABSTRACT

Described herein are high-power pulsed electromagnetic field (PEMF) applicator apparatuses. These apparatuses are configured to drive multiple applicators to concurrently deliver high-power PEMF signals to tissue. The apparatuses may be further configured to wirelessly communicate with a remote server for patient monitoring, prescription and/or device servicing.

27 Claims, 29 Drawing Sheets

Related U.S. Application Data

(60) Provisional application No. 62/647,226, filed on Mar. 23, 2018.

(56) References Cited

U.S. PATENT DOCUMENTS

| | | | |
|---|---|---|---|
| 5,314,401 | A * | 5/1994 | Tepper ............ A61N 2/02 600/15 |
| 6,132,362 | A | 10/2000 | Tepper et al. |
| 6,162,166 | A | 12/2000 | Neuwirth |
| 6,174,276 | B1 | 1/2001 | Blackwell |
| 6,261,221 | B1 | 7/2001 | Tepper et al. |
| 6,334,069 | B1 | 12/2001 | George et al. |
| 6,443,883 | B1 | 9/2002 | Ostrow et al. |
| 6,463,336 | B1 | 10/2002 | Mawhinney |
| 6,967,281 | B2 | 11/2005 | George et al. |
| 6,974,961 | B1 | 12/2005 | George et al. |
| 7,907,701 | B2 | 3/2011 | Anderson |
| 8,195,287 | B2 | 6/2012 | Dacey et al. |
| 9,024,746 | B2 | 5/2015 | Burbank et al. |
| 10,245,439 | B1 | 4/2019 | Schwarz et al. |
| 10,263,466 | B2 | 4/2019 | Boys et al. |
| 10,441,807 | B2 | 10/2019 | Moffett |
| 10,773,094 | B1 | 9/2020 | Rzasa et al. |
| 11,207,541 | B2 | 12/2021 | Kirk et al. |
| 11,458,327 | B2 | 10/2022 | Kirk et al. |
| 11,547,848 | B2 | 1/2023 | Babico |
| 11,771,913 | B2 | 10/2023 | Kirk et al. |
| 2004/0176805 | A1 | 9/2004 | Whelan et al. |
| 2004/0210254 | A1 | 10/2004 | Burnett et al. |
| 2005/0010163 | A1 | 1/2005 | Aoki et al. |
| 2005/0059153 | A1 | 3/2005 | George et al. |
| 2007/0060981 | A1 | 3/2007 | Pilla et al. |
| 2008/0004904 | A1 | 1/2008 | Tran |
| 2008/0249350 | A1 | 10/2008 | Marchitto et al. |
| 2009/0228071 | A1 | 9/2009 | Bourget |
| 2011/0065976 | A1 | 3/2011 | Chomenky et al. |
| 2011/0112352 | A1 | 5/2011 | Pilla et al. |
| 2011/0196365 | A1 * | 8/2011 | Kim ............ A61B 18/1815 606/33 |
| 2012/0116149 | A1 | 5/2012 | Pilla et al. |
| 2012/0302821 | A1 * | 11/2012 | Burnett ............ A61N 1/36021 600/13 |
| 2013/0006039 | A1 | 1/2013 | Sadler |
| 2013/0190599 | A1 * | 7/2013 | Wyeth ............ A61B 5/7282 600/409 |
| 2013/0245486 | A1 | 9/2013 | Simon et al. |
| 2014/0012108 | A1 | 1/2014 | McPeak |
| 2014/0148870 | A1 | 5/2014 | Burnett |
| 2014/0213844 | A1 | 7/2014 | Pilla et al. |
| 2014/0249355 | A1 * | 9/2014 | Martinez ............ A61N 2/004 600/14 |
| 2014/0265611 | A1 | 9/2014 | Fern et al. |
| 2014/0336443 | A1 | 11/2014 | Maharaj |
| 2014/0367270 | A1 * | 12/2014 | Williamson ........ H01M 10/42 205/337 |
| 2015/0018643 | A1 * | 1/2015 | Cole ............ A61B 5/0015 600/316 |
| 2015/0297910 | A1 * | 10/2015 | Dimino ............ A42B 1/242 600/14 |
| 2016/0015995 | A1 | 1/2016 | Leung et al. |
| 2016/0346561 | A1 * | 12/2016 | Ron Edoute ...... A61N 1/328 |
| 2017/0080245 | A1 * | 3/2017 | Dimino ............ A42B 1/242 |
| 2018/0001102 | A1 | 1/2018 | Henry et al. |
| 2018/0043174 | A1 | 2/2018 | Gurfein |
| 2018/0071545 | A1 | 3/2018 | Saitoh et al. |
| 2018/0126185 | A1 * | 5/2018 | Hochstenbach ...... A61N 2/02 |
| 2018/0318598 | A1 | 11/2018 | Russo et al. |
| 2019/0126036 | A1 | 5/2019 | Franco-Obregon et al. |
| 2019/0192873 | A1 | 6/2019 | Schwarz et al. |
| 2019/0217090 | A1 | 7/2019 | Ryaby et al. |
| 2019/0290925 | A1 | 9/2019 | Gellman et al. |
| 2020/0001101 | A1 | 1/2020 | Moffett |
| 2020/0139120 | A1 | 5/2020 | Rajguru et al. |
| 2020/0234811 | A1 | 7/2020 | Greenspan et al. |
| 2020/0360710 | A1 | 11/2020 | Anderson et al. |
| 2021/0085180 | A1 | 3/2021 | Jung et al. |
| 2021/0121711 | A1 | 4/2021 | Babico |
| 2022/0379131 | A1 | 12/2022 | Elsiminger et al. |
| 2022/0392608 | A1 | 12/2022 | Ferrer Herrera et al. |
| 2022/0409917 | A1 | 12/2022 | Kirk et al. |
| 2023/0069770 | A1 | 3/2023 | Babico |
| 2024/0139536 | A1 | 5/2024 | Babico |

OTHER PUBLICATIONS

Apfelbaum et al.; Postoperative pain experience: results from a national survey suggest postoperative pain continues to be undermanaged; Anesthesia and Analgesia; 97(2); pp. 534-540; Aug. 2003.

Baranano et al.; Biliverdin reductase: a major physiologic cytoprotectant; Proceedings of the National Academy of Sciences; 99(25); pp. 16093-16098; Dec. 10, 2002.

Basbaum et al.; Cellular and molecular mechanisms of pain; Cell; 139(2); pp. 267-284; Oct. 16, 2009.

Brennan et al.; Cytokine expression in chronic inflammatory disease; British Medical Bulletin; 51(2); pp. 368-384; Apr. 1995.

Buckley et al.; The resolution of inflammation; Nature Reviews Immunology; 13(1); pp. 59-66; Jan. 2013.

Catala; Five decades with polyunsaturated Fatty acids: chemical synthesis, enzymatic formation, lipid peroxidation and its biological effects; Journal of Lipids; http://dx.doi.org/10.1155/2013/710290; 20 pages; (the year of publication is sufficiently earlier than the effective U.S. filing date and any foreign priority date so that the particular month of publication is not in issue) 2013.

Clark et al.; Neuropathic pain and cytokines: current perspectives; Journal of Pain Research; 6; pp. 803-814; doi: 10.2147/JPR.S53660; 12 pages; Nov. 21, 2013.

Commins et al.; The extended IL-10 superfamily: IL-10, IL-19, IL-20, IL-22, IL-24, IL-26, IL-28, and IL-29; Journal of Allergy and Clinical Immunology; 121(5); pp. 1108-1111; May 2008.

Dutra et al.; Heme on innate immunity and inflammation; Frontiers in Pharmacology; 5; Article 115; doi: 10.3389/fphar.2014.00115; 20 pages; May 2014.

Gou et al.; Meta-analysis of clinical efficacy of pulsed radio frequency energy treatment; Annals of Surgery; 255(3); pp. 457-467; Mar. 2012.

Greene et al.; Regulation of inflammation in cancer by eicosanoids; Prostaglandins and Other Lipid Mediators; 96(1-4); pp. 27-36; 26 pages; (Author Manuscript); Nov. 2011.

Guo et al.; Pulsed radio frequency energy (PRFE) use in human medical applications; Electromagnetic Biology and Medicine; 30(1); pp. 21-45; Mar. 2011.

Hasegawa et al.; Modifying TNF alpha for therapeutic use: a perpective on the TNF receptor system; Mini Reviews in Medicinal Chemistry: 1(1); pp. 5-16; May 2001.

Haworth et al.; Resolving the problem of persistence in the switch from acute to chronic inflammation; Proceedings of the National Academy of Sciences; 104(52); pp. 20647-20648; Dec. 26, 2007.

He et al.; Exposure to extremely low-frequency electromagnetic fields modulates Na+ currents in rat cerebellar granule cells through increase of AA/PGE2 and EP receptor-mediated cAMP/PKA pathway; Plos One; 8(1); pp. e54376; 13 pages; Jan. 22, 2013.

Heden et al.; Effects of pulsed electromagnetic fields on postoperative pain: a double-blind randomized pilot study in breast augmentation patients; Aesthetic Plastic Surgery; 32(4); pp. 660-666; Jul. 2008.

Ji et al; Emerging roles of resolvins in the resolution of inflammation and pain; Trenads in Neurosciences; 34(11); pp. 599-609; 20 pages; (Author Manuscript); Nov. 2011.

Kunkel et al.; Suppression of acute and chronic inflammation by orally administered prostaglandins; Arthritis and Rheumatism: Official Journal of the American College of Eheumatology; 24(9); pp. 1151-1158; Sep. 1981.

Livak et al.; Analysis of relative gene expression data using real-time quantitative PCR and the 2-??CT method; Methods; 25(4); pp. 402-408; Dec. 2001.

Markov et al.; Interaction between electromagnetic fields and the immune system: possible mechanisms for pain control; Ayrapetyan

(56) References Cited

OTHER PUBLICATIONS

SNM, M.S., ed.; Bioelectromagnetics Current Concepts; Dordrecht: Springer; pp. 213-225; (the year of publication is sufficiently earlier than the effective U.S. filing date and any foreign priority date so that the particular month of publication is not in issue) 2006.
McIntyre et al.; Molecular mechanisms of early inflammation; Thromb Haemost; 78(I):302-305; Jul. 1997.
Medzhitov et al.; Transcriptional control of the inflammatory response; Nature Reviews Immunology; 9(10); pp. 692-703; Oct. 2009.
Medzhitov: Origin and physiological roles of inflammation; Nature; 454 (7203); pp. 428-435; Jul. 23, 2008.
Medzhitov; Inflammation 2010: new adventures of an old flame; Cell; 140(6); pp. 771-776; Mar. 19, 2010.
Moffett et al.; Activation of endogenous opioid gene expression in human keratinocytes and fibroblasts by pulsed radiofrequency energy fields; Journal of Pain Research; 5; pp. 347-357; Sep. 19, 2012.
Moffett et al.; Pulsed radio frequency energy field treatment of cells in culture results in increased expression of genes involved in angiogenesis and tissue remodeling during wound healing; The Journal of Diabetic Foot Complications; 3(2); pp. 30-39; (the year of publication is sufficiently earlier than the effective U.S. filing date and any foreign priority date so that the particular month of publication is not in issue) 2011.
Moffett et al.; Pulsed radio frequency energy field treatment of cells in culture results in increased expression of genes involved in inflammation phase of lower extremity diabetic wound healing; The Journal of Diabetic Foot Complications; 2(3); pp. 57-64; (the year of publication is sufficiently earlier than the effective U.S. filing date and any foreign priority date so that the particular month of publication is not in issue) 2010.
Moreland; Inhibitors of tumor necrosis factor for rheumatoid arthritis; 66(6); pp. 367-374; Jun. 1999.
MORELAND; Inhibitors of tumor necrosis factor for rheumatoid arthritis; The Journal of Rheumatology; 57; pp. 7-15; May 1, 1999.
Mosser et al.; Interleukin-10: new perspectives on an old cytokine; Immunological Reviews; 226(1); pp. 205-218; 22 pages; (Author Manuscript); Dec. 2008.
Nathan; Nonresolving inflammation; Cell; 140(6); pp. 871-882; Mar. 19, 2010.
Neher et al.; Molecular mechanisms of inflammation and tissue injury after major trauma is complement the "bad guy"?; Journal of Biomedical Sciences; 18(1); pp. 90; doi: 10.1186/1423/1423-0127-18-90; Dec. 2011.
Novo et al.; Redox mechanisms in hepatic chronic wound healing and fibrogenesis; Fibrogenesis and tissue repair; 1(1); doi:10.1186/1755-1536-1-5; 58 pages; Dec. 2008.
Pelletier et al.; New tricks from an old dog: mitochondria) redox signaling in cellular inflammation; InSeminars in Immunology; 24(6); pp. 384-392; 21 pages; (Author Manuscript); Dec. 2012.
Pilla et al.; EMF signals and ion/ligand binding kinetics: prediction of bioeffective waveform parameters; Bioelectrochemisrty and Bioenergetics; 48(1); pp. 27-34; Feb. 1999.
Pilla et al.; Nonthermal electromagnetic fields: from first messenger to therapeutic applications; Electromagnetic Biology and Medicine; 32(2); pp. 123-136; Jun. 2013.
Pons et al.; Pro-inflammatory and anti-inflammatory effects of the stable prostaglandin D2 analogue; European Journal of Pharmacology; 261(3); pp. 237-247; Aug. 22, 1994.
Rohde et al.; Effects of pulsed electromagnetic fileds on interleukin-1 beta and postoperative pain: a double-blind, placebo-controlled, pilot study in breast reduction patients; Plastic and Reconstructive Surgery; 125(6); pp. 1620-1629; Jun. 2010.
Ross et al.; Effect of time-varied magnetic field on inflammatory response in macrophage cell line RAW 264.7; Electromagnetic Biology and Medicine; 32(1); pp. 59-69; Mar. 2013.
Ross et al.; Effect of pulsed electromagnetic field on inflammatory pathway markers in RAW 264.7 murine macrophages; Journal of Inflammation Research; 6; pp. 45-51; (the year of publication is sufficiently earlier than the effective U.S. filing date and any foreign priority date so that the particular month of publication is not in issue) 2013.
Selvam et al.; Low frequency and low intensity pulsed electromagnetic field exerts its antinflammatory effect through restoration of plasma membrane calcium; Life Sciences; 80(26); pp. 2403-2410; Jun. 6, 2007.
Serhan et al.; Anti-inflammatory and proresolving lipid mediators; Annu. Rev. Pathmechdis. Mech. Dis.; 3; pp. 279-312; 43 pages; (Author Manuscript); Feb. 28, 2008.
Serhan et al.; Maresins: novel macrophage mediators with potent anti-inflammatory and proresolving actions; Journal of Experimental Medicine; 206(1); pp. 15-23; Jan. 16, 2009.
Serhan et al.; Protectins and maresins: New pro-resolving families of mediators in acute inflammation and resolution bioactive metabolome; Biochimica et Bipphysics Acta (BBA)—Molecular and Cell Biology of Lipid; 1851 (4); pp. 397-413; 40 pages; (Author Manuscript); Apr. 30, 2015.
Serhan; Novel lipid mediators and resolution mechanisms in acute inflammation: to resolve or not ?; The American Journal of Pathology; 177(4); pp. 1576-1591; Oct. 2010.
Serhan; Novel pro-resolving lipid mediators are leads for resolution physiology; Nature; 510(7503); pp. 92-101; 24 pages; (Author Manuscript); Jun. 2014.
Cho et al.; Discovery of (2-fluoro-benzyl)-(2-methyl-2 phenethyl-2H-chromen-6-yl)-amine (KRH-102140) as an orally active 5-lipoxygenase inhibitor with activity in murine inflammation models; Pharmacology; 87(1-2); pp. 49-55; Feb. 2011.
Spite et al.; Resovins, specialized proresolving lipid mediators, and their potential roles in metabolic diseases; Cell Metabolism; 19(1); pp. 21-36; Jan. 7, 2014.
Serhan et al.; Resolving inflammation: dual anti-inflammatory and pro resolution lipid mediators; Nature Reviews Immunology; 8(5); pp. 349-361; 31 pages; (Author Manuscript); May 2008.
Stein et al.; Peripheral mechanisms of pain and analgesia; Brain Research Reviews; 60(1); pp. 90-113; 38 pages; (Author Manuscript); Apr. 2009.
Suleyman et al.; Anti-inflammatory and side effects of cyclooxygenase inhibitors; Pharmacological Reports; 59(3); pp. 247-258; May 2007.
Uddin et al.; Resolvins: natural agonists for resolution of pulmonary inflammation; Progress in Lipid Research; 50(1); pp. 75-88; 30 pages; (Author Manuscript); Jan. 31, 2011.
Vilcek; The cytokines: an overview; In: Thomson WAaMTL, ed.; The Cytokine Handbook. 4 ed. San Diego: Academic Press, Calif, USA; pp. 1-18; (the year of publication is sufficiently earlier than the effective U.S. filing date and any foreign priority date so that the particular month of publication is not in issue) 2012.
Wagener et al.; Different faces of the heme-heme oxygenase system in inflammation; Pharmacological Reviews; 55(3); pp. 551-571; Sep. 2003.
Wagener et al.; The heme-heme oxygenase system: a molecular switch in wound healing; Blood; 102(2); pp. 521-528; Jul. 15, 2003.
Wegiel et al.; Go green: the anti-inflammatory effects of biliverdin reductase; Frontiers in Pharmacology; 3; Article 47; doi: 10.3389/fphar.2012.00047; 8 pages; Mar. 16, 2012.
Xu et al.; Resolvins RvE1 and RvD1 attenuate inflammatory pain via central and peripheral actions; Nature Medicine; 16(5); pp. 591-597; 10 pages; (Author Manuscript); May 2010.
Yang et al.; Metabolomics-lipidomics of eicosanoids and docosanoids generated by phagocytes; Current Protocols in Immunology; 95(1); pp. 14-26; 36 pages; (Author Manuscript); Nov. 2011.
Yang et al.; Reactive oxygen species in the immune system; International Reviews of Immunology; 32(3); pp. 249-270; Jun. 2013.
Yeretssian et al.; Molecular regulation of inflammation and cell death; Cytokine; 43(3); pp. 380-390; Sep. 2008.
Ferrer Herrera et al.; U.S. Appl. No. 18/051,834 entitled "Wearable pulsed electromagnetic field sensing device," filed Nov. 1, 2022.
Babico et al.; U.S. Appl. No. 18/568,493 entitled "Method and apparatus for providing pulsed electromagnetic field therapy," filed Dec. 8, 2024.

\* cited by examiner

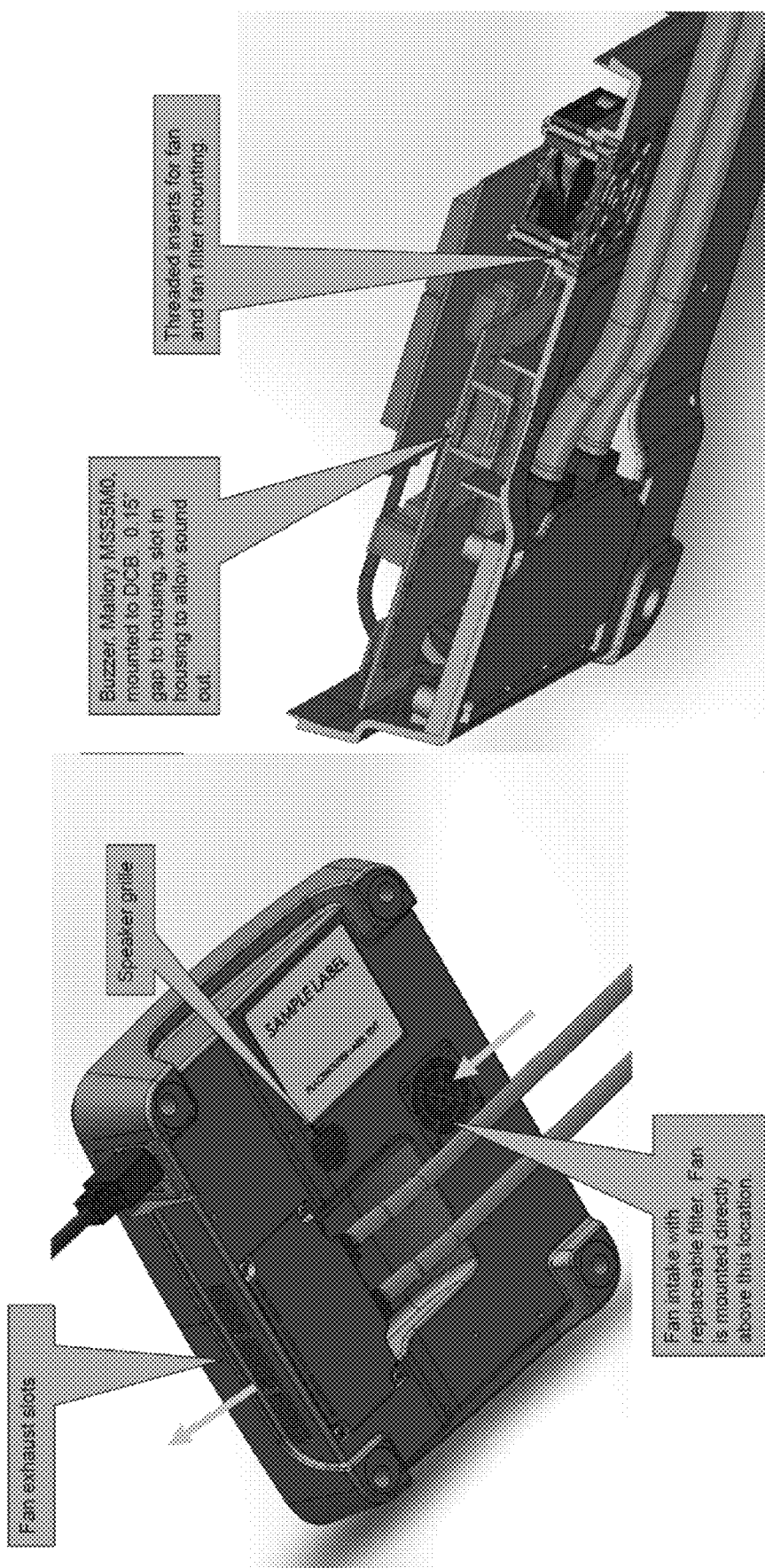

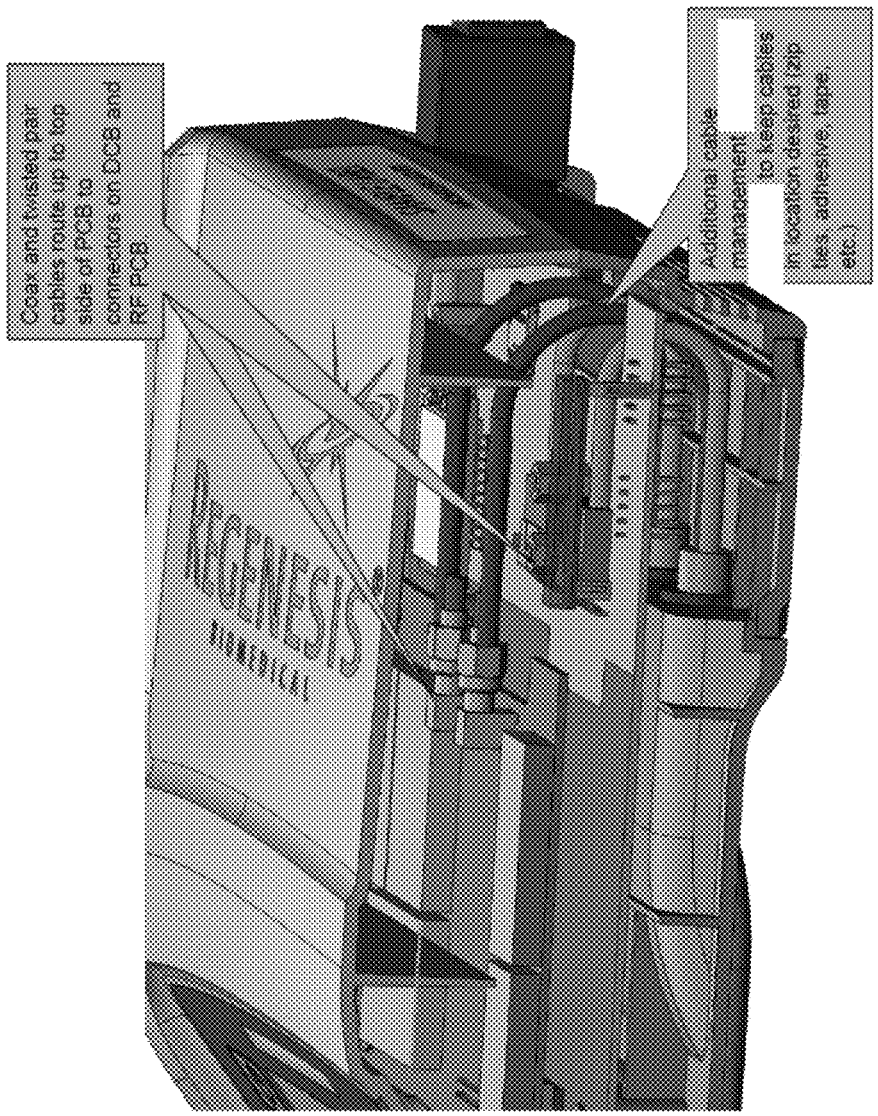
FIG. 15C
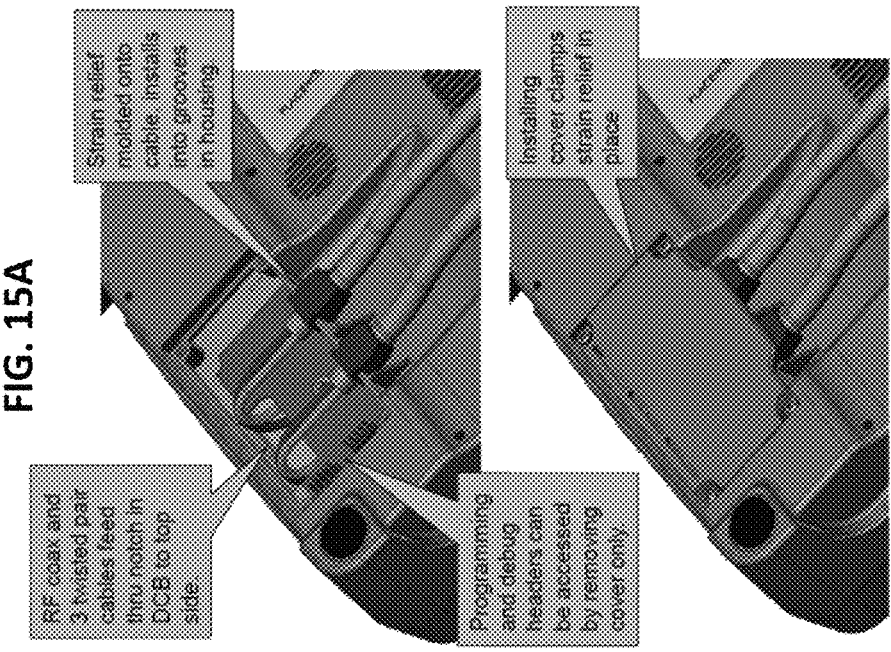
FIG. 15A
FIG. 15B

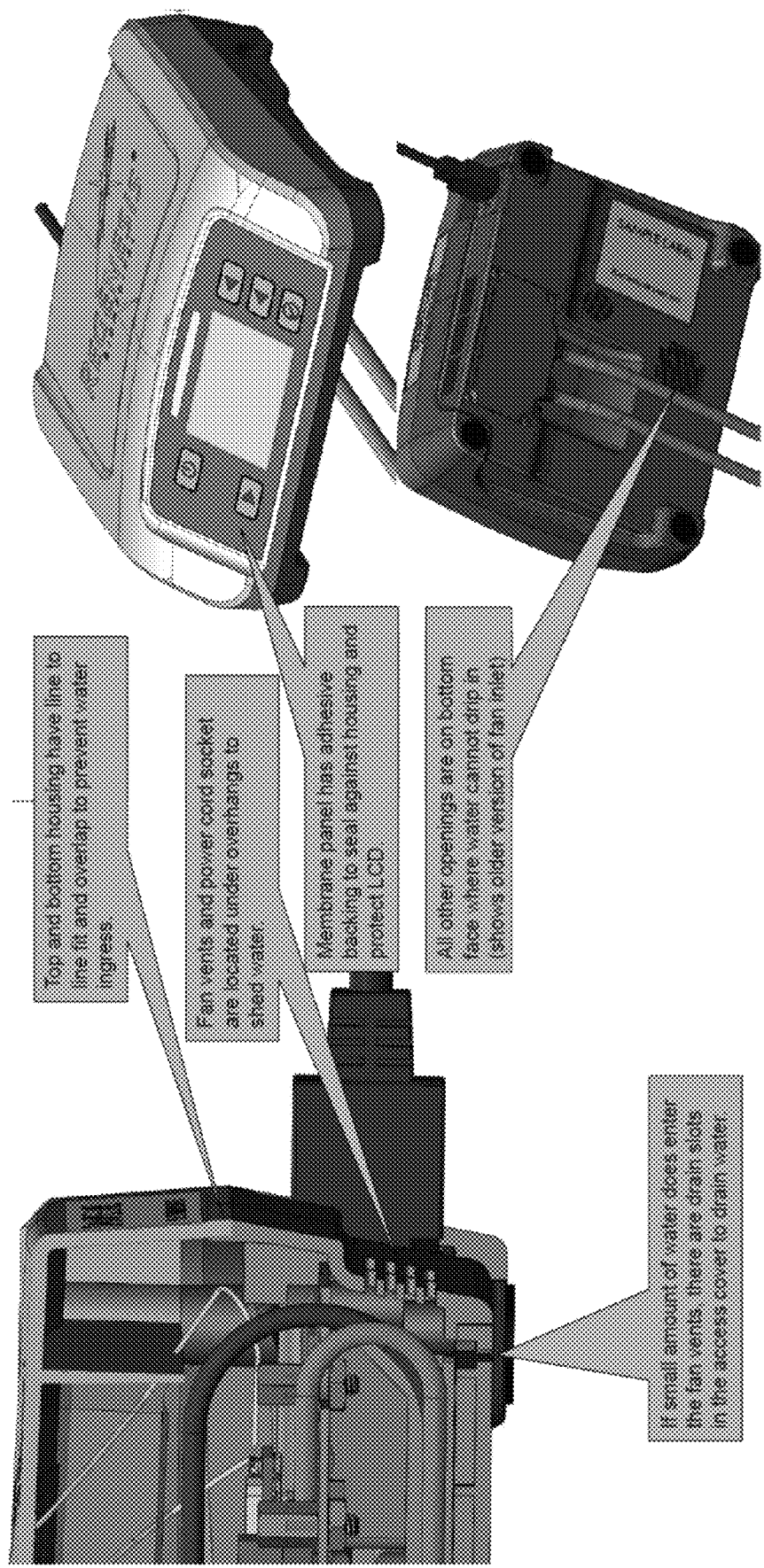

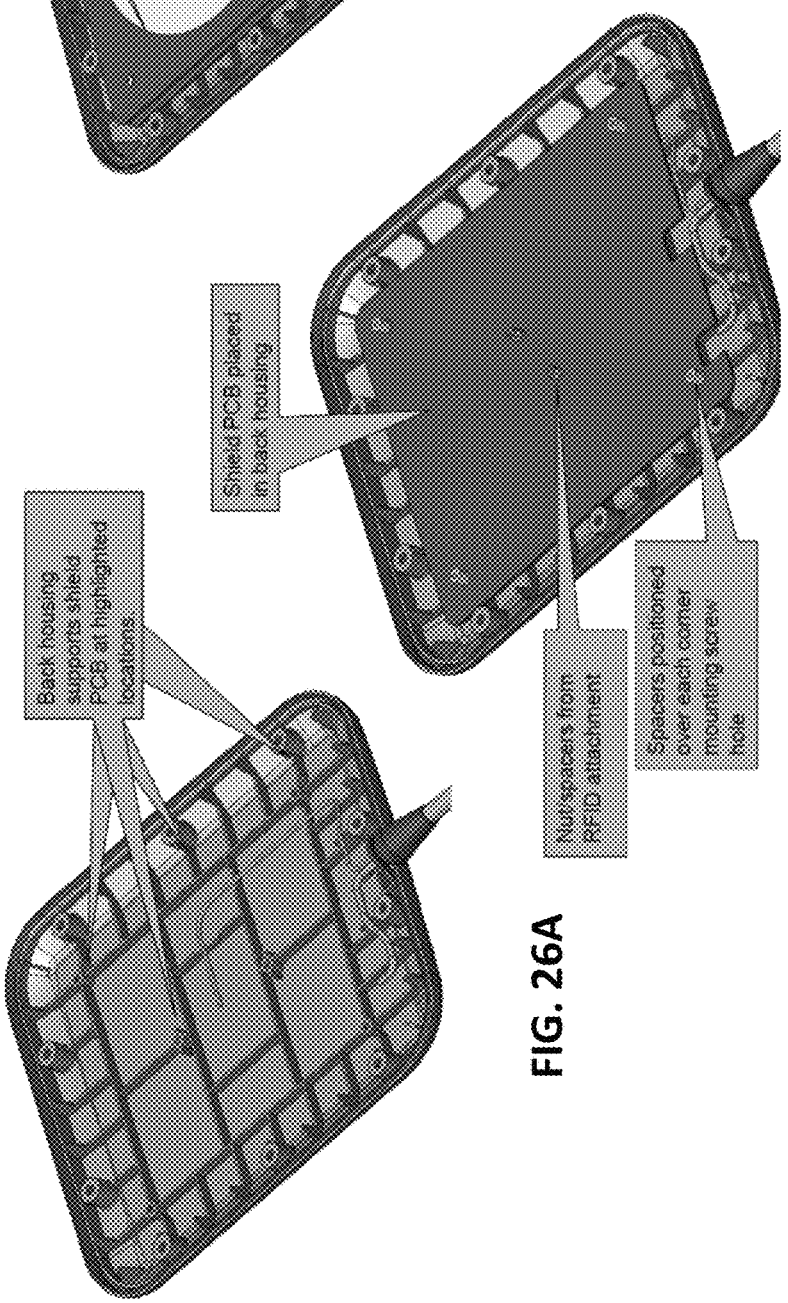
FIG. 26A
FIG. 26B
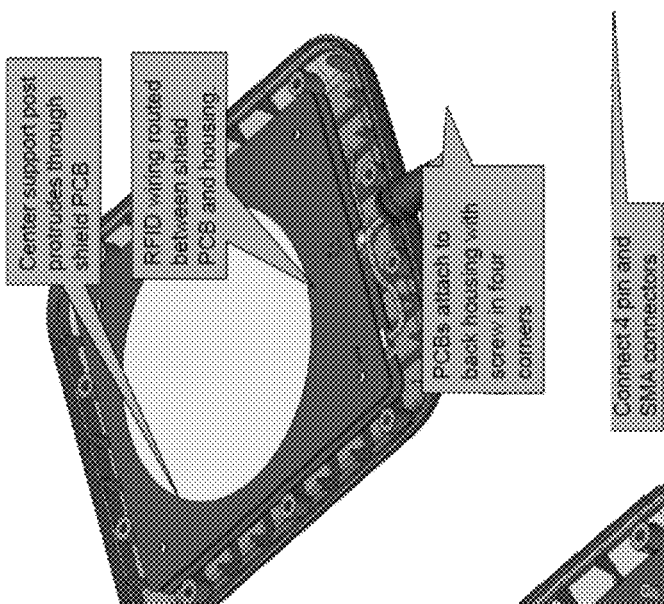
FIG. 26C

HIGH-POWER PULSED ELECTROMAGNETIC FIELD APPLICATOR SYSTEMS

CROSS REFERENCE TO RELATED APPLICATIONS

This application is a continuation of U.S. patent application Ser. No. 17/556,398, filed Dec. 20, 2021, which is a continuation of U.S. patent application Ser. No. 17/040,636, filed Sep. 23, 2020, now U.S. Pat. No. 11,207,541, titled "HIGH POWER PULSED ELECTROMAGNETIC FIELD APPLICATOR SYSTEMS", which is the national phase of International Application No. PCT/US2019/023860, filed Mar. 25, 2019, which application claims the benefit of U.S. Provisional Application No. 62/647,226, filed Mar. 23, 2018 (titled "HIGH-POWER PULSED ELECTROMAGNETIC FIELD APPLICATOR SYSTEMS"), all of which are herein incorporated by reference in their entirety.

The following U.S. patent applications are herein incorporated by reference in their entirety to the same extent as if each individual publication or patent application was specifically and individually indicated to be incorporated by reference: U.S. Pat. No. 6,334,069, titled "PULSED ELECTROMAGNETIC ENERGY TREATMENT APPARATUS AND METHOD", filed Jan. 15, 1999, U.S. Pat. No. 6,353,763, titled "PULSED ELECTROMAGNETIC ENERGY TREATMENT APPARATUS AND METHOD", filed Jun. 27, 2000, U.S. Pat. No. 6,967,281, titled "COVER FOR ELECTROMAGNETIC TREATMENT APPLICATOR", filed Oct. 22, 2003, U.S. Pat. No. 6,974,961, titled "COVER FOR ELECTROMAGNETIC TREATMENT APPLICATOR", filed Sep. 14, 2000, U.S. Pat. No. 7,024,239, titled "PULSED ELECTROMAGNETIC ENERGY TREATMENT APPARATUS AND METHOD", filed Nov. 20, 2001, and PCT Patent Application No. PCT/US2015/062232, titled "TREATMENT OF CONDITIONS SUSCEPTIBLE TO PULSED ELECTROMAGNETIC FIELD THERAPY", filed Nov. 23, 2015.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure relates generally to pulsed electromagnetic field (PEMF) systems, apparatuses and methods. In particular, the disclosure relates to high-power pulsed electromagnetic field (PEMF) applicator systems.

BACKGROUND

Pulsed electromagnetic fields (PEMF) have been described for treating therapeutically resistant problems of both the musculoskeletal system as well as soft tissues. PEMF typically includes the use of low-energy, time-varying magnetic fields. For example, PEMF therapy has been used to treat non-union bone fractures and delayed union bone fractures. PEMF therapy has also been used for treatment of corresponding types of body soft tissue injuries including chronic refractory tendinitis, decubitus ulcers and ligament, tendon injuries, osteoporosis, and Charcot foot. During PEMF therapy, an electromagnetic transducer coil is generally placed in the vicinity of the injury (sometimes referred to as the "target area") such that pulsing the transducer coil will produce an applied or driving field that penetrates to the underlying tissue.

Treatment devices emitting magnetic and/or electromagnetic energy offer significant advantages over other types of electrical stimulators because magnetic and electromagnetic energy can be applied externally through clothing and wound dressings, thereby rendering such treatments completely non-invasive. Moreover, published reports of double blind placebo-controlled clinical trials utilizing a RF transmission device (Diapulse) suggest that this ancillary treatment device significantly reduces wound healing time for chronic pressure ulcers as well as for surgical wounds. Studies using Dermagen, a magnetic device manufactured in Europe which produces a low frequency magnetic field, have demonstrated significant augmentation of healing of venous stasis ulcers. Additionally, it has been shown that 50% fewer patients treated with electromagnetic energy develop reoccurring pressure ulcers, compared to control patients, suggesting that electromagnetic energy treatments impart some resistance to the reoccurrence of chronic wounds, such as pressure ulcers. Electromagnetic energy may also be useful as a preventative strategy. Analysis of the effects of electromagnetic energy on the treatment of pressure ulcers show that this treatment, by reducing healing time by an average of 50%, results in significant reductions in the costs associated with wound management.

Most PEMF transducers use a substantial amount of energy, and typically generate this energy in a base or controller portion, which may include batteries and/or a connection to a wall power source. The energy is typically conditioned or modulated into an appropriate signal and then transmitted (e.g., via a cable) to an applicator. This may make the systems expensive, and in some variations, heavy. The weight of the PEMF apparatus is generally proportional to the size of the power supply (in some cases, batteries) used to power the electrical circuitry as well as by the windings used to generate the output signal. Patient comfort while using such devices is often inversely proportional to the weight.

In particular, for high-power apparatuses (e.g., apparatuses that deliver over 40 W or greater than 100 V or energy), the generator portion is typically disposed in the base in a housing, and the pulsed high power electromagnetic energy is transferred to the applicator by a cable. This is conceptually simple, and allows efficient control of the energy to be applied. However, there are disadvantages, particularly when transferring high-energy signals on one or more cables.

Described herein are high-power PEMF applicator systems that may reduce high power electromagnetic energy leakage and may increase treatment efficiency.

SUMMARY OF THE DISCLOSURE

In general, described herein are high-power pulsed electromagnetic field (PEMF) applicator apparatuses (e.g., devices and systems, including applicators and base units with or without applicators). These apparatuses may include a base unit that includes controller that may couple to one or more applicators. In particular, described herein are apparatuses that are configured to operate a plurality of different applicators from a single base unit by efficiently multiplexing the signal, controlling (including in some variations, with feedback control) and applying high-voltage PEMF from multiple applicators without interfering with the PEMF applied by different applicators.

For example, described herein are high-power pulsed electromagnetic field (PEMF) applicator systems that may include: a base housing comprising a controller configured to generate and multiplex a high-power pulsed signal; and two or more applicators coupled to the base, each applicator comprising: a coil circuit configured to emit the high-power pulsed electromagnetic field signal wherein the high-power pulsed electromagnetic field signal has a power of greater than 40 W; and an electromagnetic energy shield disposed between the drive circuitry and the coil circuit; wherein the two or more controllers are configured to apply the multiplexed signal to the two or more applicators so that each applicator emits a PEMF signal without interference.

The two or more applicators are configured to be handheld. As will be described in greater detail below, the two or more applicators may include a feedback circuit positioned behind the coil circuit and configured to detect the field strength of the high-power pulsed electromagnetic field signal emitted by the coil circuit. The controller may be configured to adjust an amplitude of the high-power pulsed electromagnetic field in response to the detected filed strength (e.g., one or more of electric field, magnetic field, or both) by adjusting a control signal (e.g., a low-power control signal), to adjust an RF amplification stage that is connected to, or part of, the controller.

The feedback circuit may be printed on a first side of a printed circuit board and the coil circuit may be printed on an opposite side of the printed circuit board.

In general, each applicator of the one or more applicators may include a tuning/matching circuit. The applicator may be tuned to a specific body part (e.g., head, food, arm, hand, torso, upper chest, belly, back, leg, ankle, wrist, etc.).

Any appropriate PEMF signal may be applied. For example, the high-power pulsed electromagnetic field signal may have a carrier frequency in the MHz range. For example, the carrier frequency may be between about 8 MHz and 100 MHz (e.g., about 27 MHz, about 10 MHz, between about 10 MHz and 60 MHz, etc.).

Any of the controllers may include a diagnostic unit configured to run diagnosis and generate an error code. Any of the apparatuses, and including any of the controllers of the apparatus, may include a wireless circuitry (e.g., a cellular circuitry or module, Wi-Fi, ZigBee, etc.), configured to wirelessly communicate with a remote server. In some variations the controller further comprises a radio frequency identification (RFID) reader. The one or more applicators may be identified by an RFID code that may be read by the reader.

The high-power pulsed signal may be multiplexed between the two or more applicators in any appropriate manner. For example, each applicator may be connected to an RF amplification stage that receives an activation signal from the controller; when activated by the activation signal, the RF amplification stage transmits the current portion of the high-power pulsed signal to the associated applicator coupled to that RF amplification stage. The controller may activate only one RF amplification stage at a time in this manner. Alternatively, the controller may address portions of the a high-power pulsed signal and each applicator or the associated RF amplification stages may be configured to apply only the a high-power pulsed signal that includes an associated address (e.g., the high-power pulsed signal or a separate signal concurrently transmitted may comprises an address unique to each of the one or more applicators), and in some variations, the applicators may comprise or connect to an address decoder or switch.

In general, the applicators may include a shield board configured to shield one side of the coil circuit. The applicator and/or base may be arranged so that the high-voltage RF energy associated with the RF amplification stages (in the base) and applicators do not interfere (inductively, capacitively, or otherwise) with the operation of the electronics in the device.

As mentioned, any of the apparatuses described herein may be configured to drive one or more applicators that are load-specific. In general, the apparatuses described herein include a tuned switching power amplifier comprising a single-pole switching element that is capable of very efficient operation. These tuned switching power amplifiers may be class-E amplifiers. To avoid load sensitivity of these amplifiers, which may require a closely impedance-matched load, multiple features are described herein, which may be separately included or may be combined together. For example, described herein are applicators configured to be operated with different body treatment areas; e.g., the load profile of these different applicators may be configured to have different loads, permitting them to be impedance matched to get efficient energy transfer.

Any of the apparatuses described herein may include one or more layers between the applicator coil and the enclosure to de-Q the coil and make it less sensitive to load variation. For example, the different layers may be polyethylene foam layers. These layers may alternatively or additionally be configured to preferentially absorb some of the electric field (E-field) and thereby adjust the ratio of magnetic field (H-field) compared to the E-field. Each layer may be between about 0.1 mm and 1 cm thick (e.g., between about 0.1 mm and 5 mm, between about 0.1 mm and 3 mm, etc.) and any number of layers may be used (e.g., 1, 2, 3, 4, 5, 6, 7, 8, 9, 10, 11, etc., between 1 and 25, between 1 and 20, between 1 and 15, between 1 and 10, etc.).

Any of the apparatuses may also or alternatively be used with body-region specific applicators that are configured to be used only on certain body areas, as mentioned above. For example, a foot or a low back applicator may be specifically impedance matched for its body treatment area. This allows the (e.g., class-E) amplifier to be used for treatment on different body areas despite a wide range of potential loads. In some variations, a self-tuning amplifier circuit may be used and configured to automatically adjust to the changing therapy loads.

For example, a high-power pulsed electromagnetic field (PEMF) applicator system may include: a base housing comprising a controller configured to generate and multiplex a high-power pulsed signal, the base comprising a tuned switching power amplifier comprising a single-pole switching element configured to generate a pulsed drive signal; and two or more applicators coupled or configured to couple to the base, each applicator comprising: a coil circuit configured to emit the high-power pulsed electromagnetic field signal wherein the high-power pulsed electromagnetic field signal has a power of greater than 40 W, an enclosure around the coil circuit; and one or more layers between the applicator coil and the enclosure configured to decrease the sensitivity of the tuned switching power amplifier to load variations; wherein the two or more applicators are configured to apply the multiplexed signal to the two or more applicators so that each applicator emits a PEMF signal without interference.

As mentioned, the one or more layers may comprises one or more polyethylene foam layers. The tuned switching power amplifier may comprise a class E power amplifier. The tuned switching power amplifier may be configured, for example, to generate a drive signal comprising a carrier frequency that is about 27.12 MHz and has a stimulation pulse width of between about 1 microsecond and about 200 microseconds. The tuned switching power amplifier may be configured to generate a drive signal comprising a carrier frequency and a stimulation pulse width of between about 1 microsecond and about 200 microseconds at a pulse rate or between 0.5 kHz and 2 KHz.

In any of these variations, the two or more applicators may each have a load that is tuned to a specific body part (the same body part or different body parts). For example, the two or more applicators may each have a load that is tuned to one or more of: a hand, a foot, a leg, a lower back, a head, a neck, a chest, an arm, and a hand.

Any of these apparatuses may include a plurality of RF amplification stages in the base housing, wherein the each RF amplification stage is configured to one of the two or more applicators. Each of the RF amplification stage may be configured to receive an enabling control signal from the controller to enable application of the high-power pulsed signal by just one of the RF amplification stages.

In general, any of the applicators may include feedback that may allow control and interpretation of the operation of the applicator(s). Thus, any of the applicators may include a feedback sensor configured to receive a feedback signal from the coil circuit, and to transmit the feedback signal to an RF amplification stage connected to the applicator, wherein the feedback signal modifies operation of the RF amplification stage.

Any appropriate feedback may be received and interpreted by the applicator, RF amplification stage, controller and/or a remote processor. For example, the applicator(s) may include a feedback sensor that senses capacitive coupling. Capacitively coupled feedback may use a trace that is radially adjacent to the coil that senses an E-field through capacitive coupling to the coil. It may also sense an E-field reflected from the skin of a user, so that the measured field is the summation of both the radiated and reflected fields. Alternatively or additionally, a capacitively coupled feedback approach may sense the presence of skin independent of the field being applied.

Any of the apparatuses described herein may use digital filtering of the raw feedback from the applicator. For example, a feedback signal may be an AC signal that is coupled from the radiator. This AC signal may be half-wave rectified and RC filtered (e.g., on the applicator) such that the feedback signal that is sent to the base unit is a 42 μsec pulse that increases with an RC time constant to a peak at the end of the 42 μsec period (when the exemplary signal described above is applied by the applicator). The feedback signal may be sampled, e.g., in software, to detect a peak which is captured as a digitally converted feedback level that may then be used by the controller and/or RF amplifier stage to control the field strength signal in a closed-loop manner. This approach may allow the use of less hardware in the applicator may avoid transmitting a DC level back to the base unit, which may be more susceptible to noise pickup.

Alternatively or additionally, inductively coupled feedback may be used. For example, a feedback trace maybe positioned on a side of the coil board, opposite from the therapy coil. This may reduce capacitive coupling to both the coil and skin, and therefore make inductance the dominant sensing mechanism. This approach may reduce the false-field effect of picking up the reflected field from the user's skin.

One or more loop antennas may be used on the applicator board for inductive coupling to the H-field. This may allow us to specifically control H-field rather than simply the E-field. This approach may also give a more accurate measurement of the field strength produced because H-field is not generally reflected from the user.

Any of these sensing methods may combine both inductive and capacitive sensing. This may allow control of E- and H-fields independently from each other.

Alternatively or additionally, any of these methods and apparatuses may include optical feedback. For example, and optical emitter and receiver (e.g., an IR emitter and receiver) may be used to detect contact and/or proximity of the applicator to the users skin. This may allow the apparatus to only activate the field when the applicator is in a treatment position.

For example described herein are high-power pulsed electromagnetic field (PEMF) applicator system, the system comprising: a base housing comprising a controller configured to generate and multiplex a high-power pulsed signal, the base comprising a tuned switching power amplifier comprising a single-pole switching element configured to generate a pulsed drive signal, and a plurality of RF amplification stages; and two or more applicators coupled or configured to couple to one of the RF amplification stages of the plurality of RF amplification stages in the base housing, wherein each applicator comprises: a coil circuit configured to emit the high-power pulsed electromagnetic field signal wherein the high-power pulsed electromagnetic field signal has a power of greater than 40 W, a feedback sensor configured to receive a feedback signal from the coil circuit, and to transmit the feedback signal to the RF amplification stage connected to the applicator, wherein the feedback signal modifies the operation of the RF amplification stage to increase or decrease the intensity of the emitted high-power pulsed electromagnetic field signal, wherein the two or more applicators are configured to apply the multiplexed signal to the two or more applicators so that each applicator emits a PEMF signal without interference.

The feedback sensor may be a capacitively coupling feedback sensor (e.g., a capacitively coupling feedback sensor adjacent to the coil circuit and configured to sense the electric field through capacitive coupling to the coil and the E-field reflected from a user). The feedback sensor may be coupled to a digital filter configured to convert the sensed feedback signal to a digital signal for transmission to the RF amplification stage.

In some variations, the feedback sensor comprises an inductive sensor that is spaced from the coil circuit so as to avoid capacitive coupling to both the coil circuit and the user's skin. The inductive sensor may be configured to detect the magnetic field (H-field) emitted by the coil circuit.

The feedback sensor may be configured to sense both capacitive and inductive feedback.

Any of the apparatuses described herein may include shielding that is textured or patterned, which may increase its effectiveness. For example, any of the PCB shielding described herein may include a cross-hatched PCB (25% coverage in a cross-hatched pattern). Surprisingly, the inventors have found that a PCB with a grounded, cross-hatched copper pattern provided excellent shielding for the radiated E-field and also provided lower EMI/EMC emissions than either a copper solid plane PCB or the aluminum shield often used in many other PEMF products.

As mentioned, any of the apparatuses described herein may include wireless communication capability. For example, any of these apparatuses may include a wireless circuit or circuitry (which may be part of or controlled by the controller) and may be used to provide connectivity to a remote server, and/or for communicating with the user (including sending alerts, data, etc.) and/or for monitoring, operating and updating the system. In some variations the apparatus (e.g., system) may be configured so that patient prescriptions are provided to the device from a physician via communications (e.g., wireless, such as cellular) circuitry on the apparatus.

In some variations, the wireless circuitry may be used to upload therapy field feedback that may indicate operation of the apparatus. This operation may indicate that the apparatus is being used properly (e.g., monitoring compliance) and/or that the apparatus is in working order (e.g., monitoring to prevent miss-operation and/or problems with the system (in the software, firmware, hardware, applicator, base, etc.).

For example, any of these apparatuses may be configured to provide real-time or near real-time monitoring and feedback to users to ensure product effectiveness. The apparatus may also be configured to provide usage validation (e.g., detecting, recording and/or transmitting) when a user is operating the device as prescribed, which may be used for compliance monitoring.

The apparatuses described herein may also be configured to uploaded diagnostics that may allow remote troubleshooting of devices in the field. For example, the apparatus may be configured to download, via the wireless circuitry, one or more software updates in the field, and/or my deliver messages, including alerts, to the user, and/or may be used to deliver a digital prescription for the operation of the apparatus.

For example, also described herein are methods of controlling operation of high-power pulsed electromagnetic field (PEMF) applicator system, the method comprising: emitting a high-power PEMF signal having a power of greater than 40W from an applicator of the high-power PEMF applicator system, wherein the high-power PEMF applicator system includes: a controller configured to generate a high-power pulsed signal, a power amplifier configured to generate a pulsed drive signal, a wireless communication circuit, and an RF amplification stage configured to couple to the applicator, wherein the applicator includes a coil circuit configured to emit the high-power pulsed electromagnetic field signal and a feedback sensor; receiving a feedback signal in the feedback sensor from the high-power PEMF signal emitted by the applicator; transmitting a therapy field feedback signal derived from or including the feedback signal to a remote server; and transmitting, from the remote server, an alert to a user operating the high-power PEMF applicator system when the therapy field feedback signal exceeds a predetermined set of performance parameters.

Emitting may be emitting the high-power PEMF signal from a plurality of applicators coupled to the high-power PEMF applicator system.

Any of these methods may include adjusting the high-power PEMF signal emitted based on the feedback signal. For example, the method may include closed-loop adjusting of the PEMF signal emitted based on the feedback signal.

Any of these methods may include transmitting, from the remote server, a prescription for additional high-power PEMF signal. For example, the methods may include receiving one or more of: a capacitance signal and an inductance signal. Receiving the feedback signal may comprises receiving a field strength signal indicating the strength of one or more of an applied electrical field or magnetic field. Receiving the feedback signal may comprise receiving a signal indicating contact with a body part.

Transmitting may comprise transmitting via a wireless (e.g., cellular) transmission from the high-power PEMF applicator system. In any of these apparatuses, transmitting the therapy field feedback signal may comprise transmitting to a user wireless communications device and transmitting form the user wireless communications device to the remote server. Transmitting the therapy field feedback signal may comprise transmitting compliance data based on the feedback signal. Transmitting the therapy field feedback signal may comprise transmitting in real time or near real-time (e.g., with less than a 1 minute latency, less than a 30 second latency, less than a 15 second latency, less than a 10 second latency, etc.). Alternatively or additionally, transmitting the therapy field feedback signal may comprises transmitting at the start of a next session of the high-power PEMF applicator system. Any of these methods may include confirming a transmission path before transmitting the therapy field feedback signal (e.g., attempting to transmit one or more times, e.g., 2 times, 3 times, 4 times, etc.).

In general, any of the methods described herein may include metering or controlling the delivery based on a prescription or metering device. For example, the methods described herein can include the step of transmitting a radio frequency identification (RFID) address between the hand-held applicator and the base housing. The hand-held applicator may generate the high-power, pulsed electromagnetic field only after the base housing verifies the RFID address.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 8C the antenna coil is a spiral. In FIG. 8D the antenna coil is a spiral having a thickness that varies as the trace helically coils around itself. In this example, the central region is thinner and the trace gets thicker as it spirals outward. The thickness may increase continuously (e.g., from one end of the trace to the other end of the trace). The variation shown in FIG. 8D may be less sensitive to load, and may allow the apparatus to be less sensitive to load variations.

FIGS. 14A and 14B show bottom and sectional views, respectively, of a base unit of a high-power pulsed electromagnetic field (PEMF) applicator system including speaker and cooling sub-systems.

FIGS. 15A-15C illustrate cable connections for a pair of applicators for a high-power pulsed electromagnetic field (PEMF) applicator system.

FIGS. 19A-19B illustrate exemplary features for enhancing water resistance in a high-power pulsed electromagnetic field (PEMF) applicator system.

FIG. 25A shows a top perspective view; FIG. 25B is a sectional view through the RFID example.

FIG. 26A-26E illustrates the assembly of an applicator of a high-power pulsed electromagnetic field (PEMF) applicator system. FIG. 26A shows the bottom housing, to which a first PCB (FIG. 26B) is added, then a second PCB (FIG. 26C) is also added. FIG. 26D shows the addition of a foam insert into the top housing. FIG. 26E shows the addition of a gasket and the top cover, which may be secured down.

DETAILED DESCRIPTION

Figure 1:
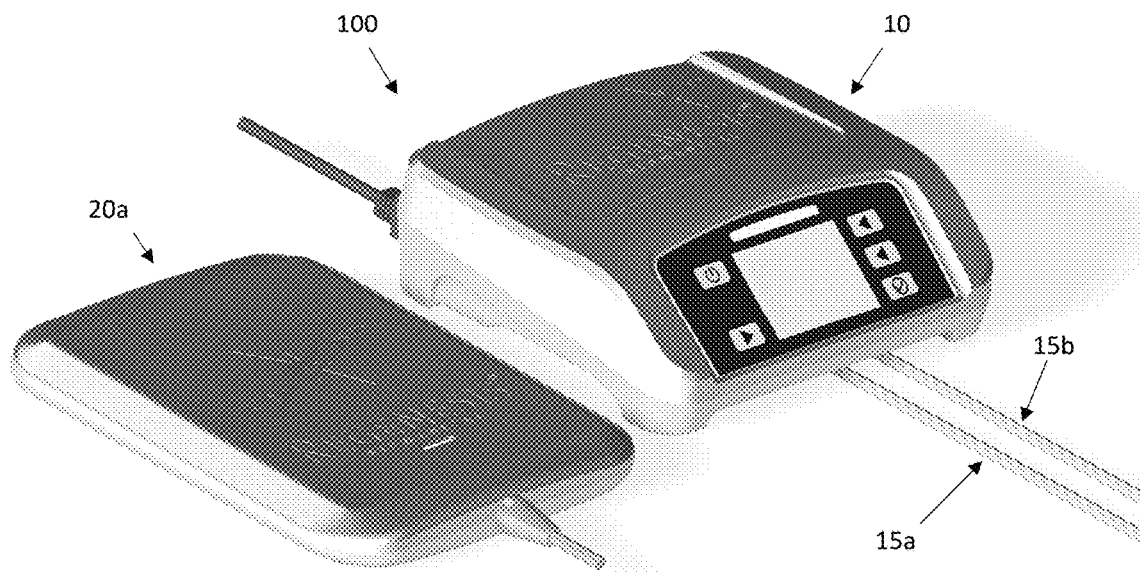
FIG. 1 illustrates one example of a high-power pulsed electromagnetic field (PEMF) applicator system including one applicator.

The present disclosure now will be described in detail with reference to the accompanying figures. This disclosure may be embodied in many different forms and should not be construed as limited to the example embodiments discussed herein.

Described herein are high-power pulsed electromagnetic field (PEMF) applicator apparatuses. In general, the apparatuses described herein are configured to as high-power pulsed electromagnetic field (PEMF) applicator apparatuses. As used herein, an apparatus may include a system and/or a method. These apparatuses may be configured as compact and lightweight apparatuses. The high-power pulsed electromagnetic field (PEMF) applicator apparatuses described herein may be further configured to have multiple applicators for simultaneously treating using the multiple applicators (e.g., dual applicators, three applicators, four applicators, five applicators, six applicators, seven applicators, eight applicators, etc.). These applicators are configured to asynchronously fire to avoid or eliminate interference between the applicators. For example, the stimulation between different applicators may be multiplexed.

Any of the high-power pulsed electromagnetic field (PEMF) applicator apparatuses described herein may be configured to provide wireless communication (via a cellular or other communications circuitry) to a remote processor and/or a telephonic or computer network. The wireless communication circuitry may permit compliance monitoring, software updates, and client messaging.

The apparatuses described herein are also configured to provide highly efficient amplification of power. These apparatuses may also be configured to prevent the build-up of potentially deleterious heat in the base unit and/or applicators. Any of the apparatuses described herein may also include a user interface (e.g., user inputs, display, etc.) that is intuitive and configured for robust operation. The user interface may also provide visual indicators of treatment and display of error conditions.

The systems can comprise a base housing including a controller configured to generate a low-power control signal and one or more applicators coupled to the base. Each applicator can include a drive circuitry comprising a generator to produce a high-power, pulsed electromagnetic field signal that is transmitted to an applicator. The high-power pulsed electromagnetic field signal can have a power of greater than 40 W.

Each applicator can further include a coil circuit configured to emit or apply the high-power pulsed electromagnetic field signal.

In general, the apparatuses described herein are configured for concurrent application of two (or more) applied high-power PEMF signals to a patient from two or more applicators. Thus, the base unit may multiplex the applied signals in a manner that prevents cross-interference between applicator fields. Typically, multiplexing may include driving multiple applicators so that applicators may each deliver non-overlapping signals. In some variations, the controller in the base unit may increase the pulsing rate by a multiple of the rate used for delivering a single applicator (e.g., if two applicators are used, the base unit may dynamically double the pulse rate, e.g., from 1000 Hz to 2000 Hz). Each RF amplification stage may receive the same pulsing signals yet be enabled independently and separately from other stages. Each applicator may then pulse at the standard rate (e.g., 1000 Hz) while alternating the application of high-power PEMF between the multiple applicators. Cross interference may be reduced or prevented by having only one applicator active at any time. The RF amplifier stages may be positioned on an RF board within the base unit, so that they may receive control signals and provide the RF pulsed output signals to the applicators. The RF amplifier stages may be controlled by one or more control signs (e.g., from the controller) that may be used to enable one stage (and therefore one amplifier) at a time. The RF amplification stages (e.g., stages 1-8 in some variations) may be addressed individually by the controller to be active, so that only one RF amplification stage having the proper address acts on it. In some variations this may be achieved by providing an enabling signal that enables individual RF amplification stages at a time. Thus, only one amplifier may be active at a time. The activation signals may be separated in time (e.g., only 42 microseconds out of 1000 microseconds). Thus, every amplification stage may receive the same signal from the controller (e.g., a signal generator portion of the controller) and this signal may be transmitted by one of the applicators only when the control signal is 'on' for that applicator, by activating the RF amplification stage in the base unit. By enabling (e.g., using enabling lines) that apparatus may not need to change anything but the rate of the signal, enabling multiplexing of the signal between different applicators.

In some variations, the apparatus may sense that one or more of the applicators is not in appropriate contact or proximity with the patient (e.g., user) and may dynamically adjust the applied signal(s).

In general, each applicator has its own feedback sensor. Thus, each applicator may be individually controlled by a feedback control loop. The feedback may sense the applied field and may be used by the RF amplification stage and/or controller to set the amplification of the applied RF energy (e.g., how much drive to apply).

In general, the apparatuses described herein may include a user display that is configured to improve display features and enhance ease of use. In addition, the apparatus may include mechanical features to improve cord management, particularly when multiple cords are used. The base unit apparatus may also include one or more features that enhance cooling of the apparatus, including internal cooling channels. These apparatuses may also include comfort-enhancing features for the applicators (e.g., beveled/sloping edges, smooth outer surface, "softer" treatment surface, etc.).

The base unit apparatus, including the controller may operate with one or more class E amplifiers per applicator, which may provide improved efficiency and allowing use of a small and lightweight switching power supply. In general, the apparatus may include an all-digital control.

Communications Circuitry

Any of the high-power pulsed electromagnetic field (PEMF) applicator systems described herein may be configured for wireless connectivity. In particular, the apparatuses described herein may be configured to include or operate with a cellular link that provides the capability to transmit compliance data (e.g., date, time, and applicator loading) for each user treatment, and/or device diagnostic data (e.g., status of power levels, display module, RFID module, memory, base unit temperature, etc.) to a remote processor, including a cloud data system. In addition to compliance monitoring, this system may allow for remote troubleshooting and error correction. The wireless (e.g., cellular) link may also allow for electronic message delivery to the client and downloading of software updates when needed. In some variations patient-specific prescriptions can be delivered wirelessly (e.g., through the cellular link) to the apparatus.

The apparatuses described herein, despite being configured to delivery very high-energy PEMF signals to multiple applicators, may be small and lightweight. In general, these apparatuses may include an embedded processor that can execute instructions and/or operate via wireless connection (e.g., cellular connection) to increase data storage and processing power, and may increase the efficiency, features and capabilities.

In some variations, the apparatus is configured to transmit information about the most recent prior use(s) upon activation (turning on) of the apparatus. For example, when the apparatus is turned on, use data (including, but not limited to compliance feedback) may be transmitted. This may allow the apparatus to adjust the next treatment (e.g., how the user is using it) based on the prior treatment data. This configuration may also provide diagnostic data, which may be used to indicate that the unit is functioning properly. For example, if the prior use data indicates that the unit is compromised, it may indicate that it should be replaced, and may be replaced immediately and/or may transmit information to the party responsible for maintaining the unit to replace or service it. In some variations the unit may present a message or messages to the user, either via the screen on the unit, or by calling or messaging (e.g., text messaging) the user with feedback, such as instructions to call the servicing party (including contact information for the servicing party).

In any of these apparatuses, the device may be configured to transmit the prior session at the start of the next treatment and may suspend or prevent the start of treatment until the data has either been transmitted or until at least some minimum number of attempts (e.g., 2 attempts, 3 attempts, 4 attempts, etc.) have been made, before the apparatus is released to allow treatment. Failed attempts may be collected and transmitted together later, including at the next power-up or prior to powering down.

In some variations the apparatus may be operated using a prescription service. When a prescription service is used, the unit may configured to permit delivery of a certain (predetermined) number of treatments per prescription, or a number of daily treatments for a predetermined number of days. The apparatus (e.g., controller) may be configured to display and/or otherwise indicate to the under the number of treatment days/times left, and may also be configured to indicate that the user should contact their physician or health care provider to modify or extend a prescription.

The apparatuses described herein may also be configured to automatically receive, via the wireless circuitry, software upgrades.

Load-Specific Applicators

In general, the apparatuses described herein may be configured (tuned) to operate at one or more specific load configurations. These load configurations may adjust parameters within the base unit and/or applicator. The base unit and/or applicator(s) may be configured to switch (manually and/or automatically) between different load configurations. For example, the base unit and/or applicator may be configured to apply the high-energy PEMF to a specific body part (e.g., a patient's foot, arm, knee, hand, torso, leg, etc.). Thus, although the apparatuses described herein may trade off load sensitivity with compact and lightweight features, this tradeoff may be ameliorated by switching between load parameters. For example, an applicator may be specifically tuned for use on a human foot. Thus, in this configuration, the load range may be set within a predefined range. The range may be set empirically, and may be set (via hardware/firmware, etc.) or switched from a look-up table. The range may be determined initially be sampling a population of people to determined expected loads on that body part.

In some variations of the apparatuses and methods described herein, the applicator may be configured with a helical antenna coil, rather than a uniform spiral coil. In some variations the helical coil comprises a trace that spirals around itself but changes diameter, getting wider as it circles outward (see, e.g., FIG. 8D). This spiral may be, in some variations, a logarithmic spiral. In some variation the space between the adjacent lines of the spiraling trace is constant while the thickness of the trace increases. In some variations the spacing between the adjacent lines of the trace varies. Thus, in any of the apparatuses described herein the applicator antenna coil may be a helical coil in which the coil starts thinner in middle and gets bigger as you circle out. This configuration may minimize the effect of the loading on the applicator.

In some configurations the load configurations of the applicator is adapted to be used with a particular body part. For example, the applicator may be configured to be applied specifically to a foot, hand, head, neck, arm, wrist, leg, torso, knee, etc.

For example, in some variations the applicator is configured to have a load that is adapted to be approximately 50 ohms, so that, when driven by the base unit, the applicator sees a load of about 50 ohm real and 0 imaginary; specifically, the cable connecting the applicator to the base unit should see about 50 ohms real and 0 imaginary. The voltage standing wave ratio (VSWR) may be less than about 2.0, and the load characteristics of the applicator may be configured so that the applicator is tuned to the expected load. If the applicator is applied to the wrong load (e.g., to a different body part), then then the apparatus may indicate that the applicator is not in contact with the correct body part. For example, the applicator may indicate that no load (if in air) or that an incorrect body part (e.g., "not the foot") than the body part for which the load was tuned in the applicator (e.g., an applicator, etc.).

In general, any of the apparatuses described herein may be configured to monitor the load seen by the applicator. This may be accomplished by measuring field strength. The sensed field strength may be used to set the drive level. If the applicator is applied outside of the select range, the apparatus may give a feedback error. For example, if the apparatus sees the wrong load (e.g., when an applicator tuned for a foot is applied to a lower back, for example), the load is mismatched, and the efficiency of the field will be outside of a predicted range, which may result in the apparatus indicating an error. Thus, the apparatus may, but does not need to specifically measure the load, but may instead use the field strength. If the load is mismatched, the field strength will be outside of the expected range and the apparatus may have to drive harder to try and achieve the target field strength. This may therefore result in an error, as described above, including an indication that the applicator is being applied to the incorrect body region (or is in air). This message may be presented to the user (e.g., on the output of the base unit) and/or may be stored and/or transmitted, and may be used for patient monitoring (e.g., compliance monitoring). For example, if there is a no-load condition on the apparatus, the apparatus may determine if the device is actually being used (or is in air), or is being used correctly. This may indicate compliance information.

In general, the apparatuses described herein may be configured for compliance monitoring. For example, the apparatus may report back information about the use, including the duration of operation, the field strength applied, the time of day, number of times/day used, etc. This data may be stored on the apparatus and/or transmitted to a remote processor/server for further analysis and/or for reporting to the patient's physician (or to a patient's medical record). Compliance monitoring may provide feedback values (digital and/or analog) that may be transmitted back via a data link, such as the wireless (e.g., cellular) data link. This compliance data may indicate when the user turned the apparatus on, what the load on the apparatus was and/or if this load was appropriate for the expected tissue (and/or if it corresponded to air, or some other tissue). Thus, the compliance data may indicate that the apparatus was turned on, and/or if the apparatus was used.

In some variations some or all of the use (or compliance) information may be transmitted to the apparatus manufacturer or distributer or any other party responsible for maintenance of the apparatus. For example, the apparatus may indicate that the device is not being operated within desired parameters, or the device is not operating properly, or that the user is not operating the device properly. In some variations the base unit may process this information, which may be analyzed locally (in the base unit) and/or remotely (e.g., in a remote processor) to determine if a technician should review the apparatus. For example, one or more use conditions may trigger contact with the party responsible for maintenance of the apparatus, who may receive a notification directly from the apparatus (e.g., via the wireless connection in the apparatus) or indirectly (via a remote processor). For example, if the apparatus determined from the use data that the load is not within the expected range during operation of the apparatus, the apparatus may use the cellular module to contact the party responsible for maintaining the apparatus; a technician may then contact the user to investigate what is going on. Similarly, the device may report an error if one the onboard peripheral devices fails to communicate serially with the processor such as the LCD Display, Cellular Modem, RFID Module, or Real Time Clock. Additionally, a micro SD card that fails or contains invalid calibration data or an RF Board voltage regulator failure may report an error.

In general, the apparatuses described herein are configured to drive more than one applicator, including two (dual applicators) or more. In some variations, the apparatuses described herein are configured to provide high-power PEMF in which the ratio of the H-field to the E-field being applied is different. For example, H-field may be greater than the E-field seen by the tissue from the applicators described herein. The antenna of the applicator may include one or more materials that reduce the E-field preferentially compared to the H-field. In some cases materials that are absorptive to E-field but not H-field may be placed between the applicator radiator coil and the patient treatment surface in order to reduce the H- to E-field ratio.

The inventors have found that relatively lower E-field (higher H-field) may have a statistically significant effect on the tissue. For example the application of energy seen by the tissue that has a greater than 50% H-field (a ratio of H-field to E-field of greater than 1), such as a greater than about 60% H-field, greater than about 65% H-field, greater than about 70% H-field, greater than about 75% H-field, greater than 80% H-field, etc. Even the lower E-field application of energy (e.g. less than 40%, less than 30%, less than 25%, less than 20%, etc.) the relatively higher H-field application of energy shows a statistically significant response. Thus, varying the amount of the H-field to E-field applied (e.g., by controlling the dielectric properties and permittivity of the applicator), may be advantageous, and may also result in significant power savings (e.g., preferentially applying an H-field to E-field ration of between about 1.1× to 10× the H-field compared to E-field, such as between about 1.2× to 8×, between about 1.5× to 5×, etc.). As the E-field to H-field ratio approaches zero, the power transfer is to the tissue may be more efficient by virtue of the H-field.

The apparatuses described herein may apply energy (PEMF energy) at any appropriate carrier frequency. The carrier frequency may be, for example, approximately 27 MHz. In some variations, the carrier frequency is 27 MHz (e.g., 27.12 MHz) may be used with a stimulation pulse width of 42 microseconds (us) at a 1 kHz pulse rate; stimulation may be applied continuously for 30 min, e.g., twice a day. In this example, the higher energy applied includes and H-field of about 10 A/meter and an E-field of about 200-250 V/m.

When multiple applicators are being used, the two applicators may be synchronized for concurrent operation in a manner that does prevents interference between the two. For example, the base unit may multiplex the applied signals, as mentioned above. Thus, in operation, the apparatus may alternative high-energy PEMF between the left, then right applicators.

In general, the apparatuses described herein may include a controller that is configured for active, closed-loop operation based on the field strength. For example, the controller (processor) of the base unit may be configured for closed loop control of operation to apply high-power PEMF to one or more applicators. As mentioned above, the controller in the base unit may receive feedback based on the driven load (and/or field strength) applied. This data may be used to control operation of the apparatus. When multiple applicators are used, the controller may monitor the load and/or field strength on each applicator and may adjust the output so that multiplexing is suspended when one of the applicators is outside of the predetermined range. Alternatively, the applicator may continue multiplexing, but may suspend the application of power to the applicator that is outside of the target range (e.g., does not have an appropriate load and/or field strength). In some variations, the feedback value is a measure of the field strength; the load seen by the applicator may be derived from the field strength. Conversely the feedback may be the load, and the field strength may be derived. Thus, in some variations, field strength may be directly measured. Field strength measured may be one or both of E-field or H-field. Alternatively or additionally, the apparatus may detect capacitive coupling of the applicator (e.g., to a body part). In some variations, the apparatus may detect the field strength and may use this detected field strength to calculate the applied energy.

EXAMPLES

Figure 2:
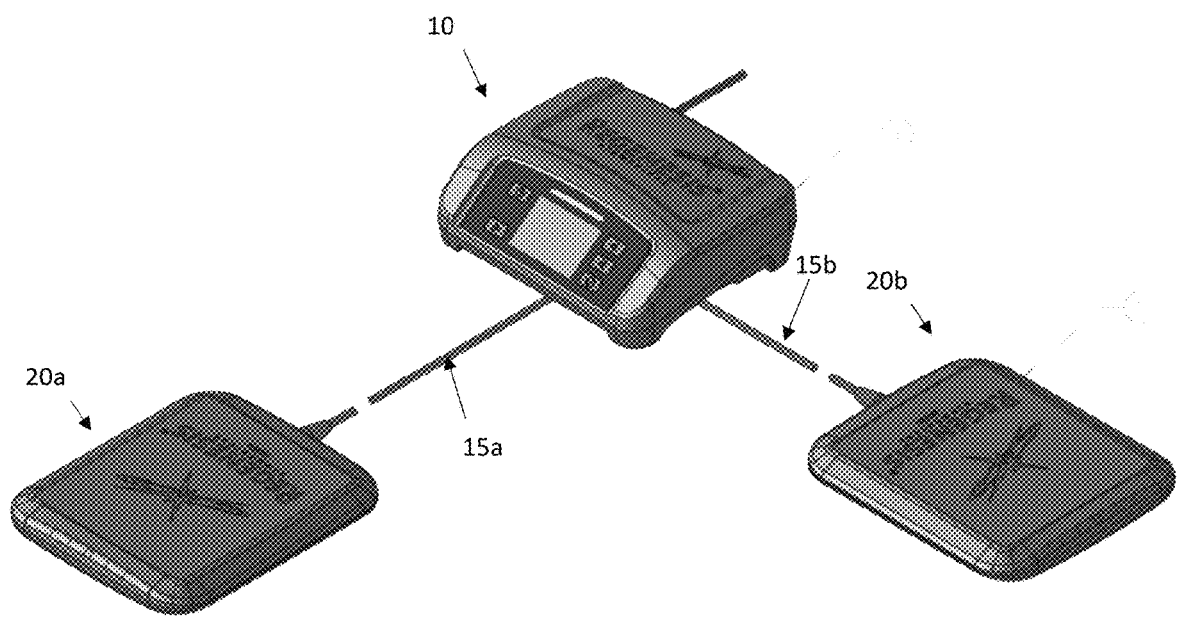
FIG. 2 shows an example of a block diagram of a high-power pulsed electromagnetic field (PEMF) applicator system including a pair of connected applicators.

FIG. 1 illustrates one example of a high-power pulsed electromagnetic field (PEMF) applicator system 100 in one embodiment. As shown in FIG. 1, the systems 100 can include a base housing 10 housing a controller (not shown in FIG. 1) that is configured to generate a low-power control signal and one or more applicators, (e.g., 20a, 20b) coupled to the base housing 10. For example, the base housing 10 is coupled to the one or more applicators (e.g., 20, 20b) by one or more cables (e.g., 15a, 15b). For example, one applicators 20a is shown in FIG. 1. FIG. 2 shows an example with two applicators 20a, 20b where the base housing 10 is coupled to the two applicators 20a and 20b a by two cables 15a and 15b.

Each applicator (e.g., 20, 20b) can apply a high-power, pulsed electromagnetic field signal based on the applied control signal, which may be multiplexed to avoid interference as described above. The high-power pulsed electromagnetic field signal can have a power of greater than 40 W on each applicator. The applicator (e.g., 20a, 20b) can further include a coil antenna circuit configured to emit or apply the high-power pulsed electromagnetic field signal. For example, the one or more applicators can be configured to be hand-held or wearable for the convenience of treatment. The one or more applicators can be applied to the back, the feet, the hand, the shoulder, or any other parts of the body of the patient.

Figure 3A:
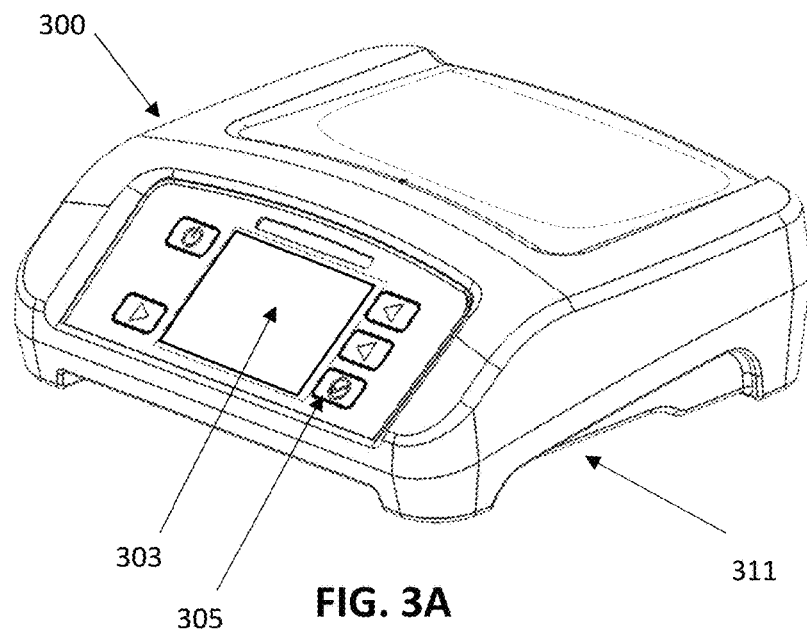
FIGS. 3A-3D schematically illustrate a base unit portion of a high-power pulsed electromagnetic field (PEMF) applicator system.
Figure 3B:
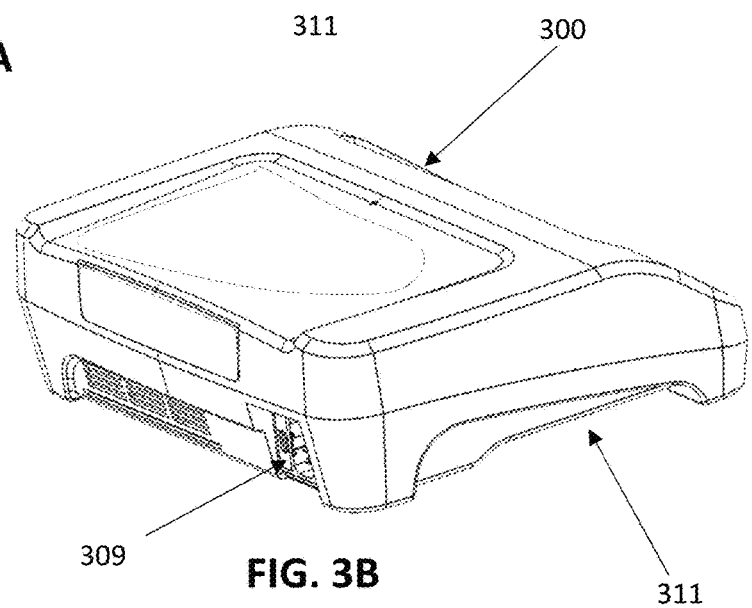
Figure 3C:
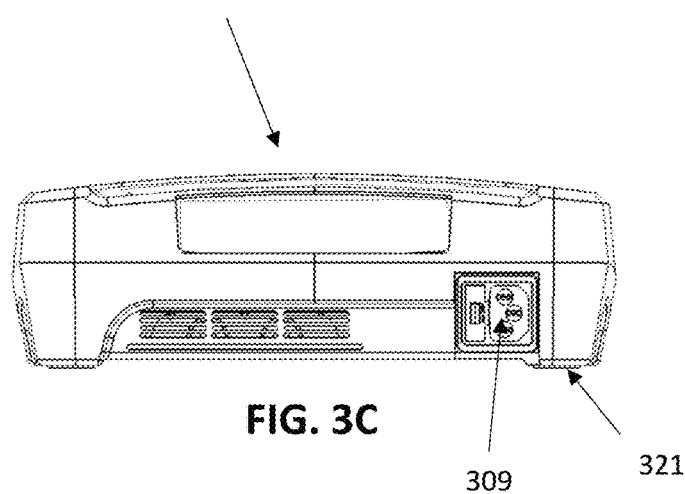

FIGS. 3A-3D illustrate an example of a base unit 300 that is configured to apply or provide high-power PEMF waveforms to one or more applicators. In FIG. 3A, the front perspective view of the base unit 300 shows a screen/display 303 and a plurality of control buttons 305. The screen may be a touch screen. The housing of the base unit may be compact, and may be configured to enhance airflow and therefore cooling of the internal components. Further, the apparatus may be ergonomically configured (having no sharp edges) and be configured to prevent water damage to the high-voltage internal components. FIG. 3B shows a back view showing connections to a power source (e.g., wall power), although other or additional power sources (battery, etc.) may be used. FIG. 3C shows a back view. The base unit may be configured to stand above the surface on which it resides by a minimum clearance of about 0.5 cm (e.g., 0.6 cm, 0.7 cm, 0.8 cm, 0.9 cm, 1.0 cm, 1.1 cm, 1.2 cm, etc.). This clearance 311 may allow air circulation for the bottom-facing fan, as well as speaker outlet. The housing may also include one or more vent inlets at or near the front top of the housing. Three or more feet 321 (four are shown in this example) may hold the bottom above the resting surface.

Figure 3D:
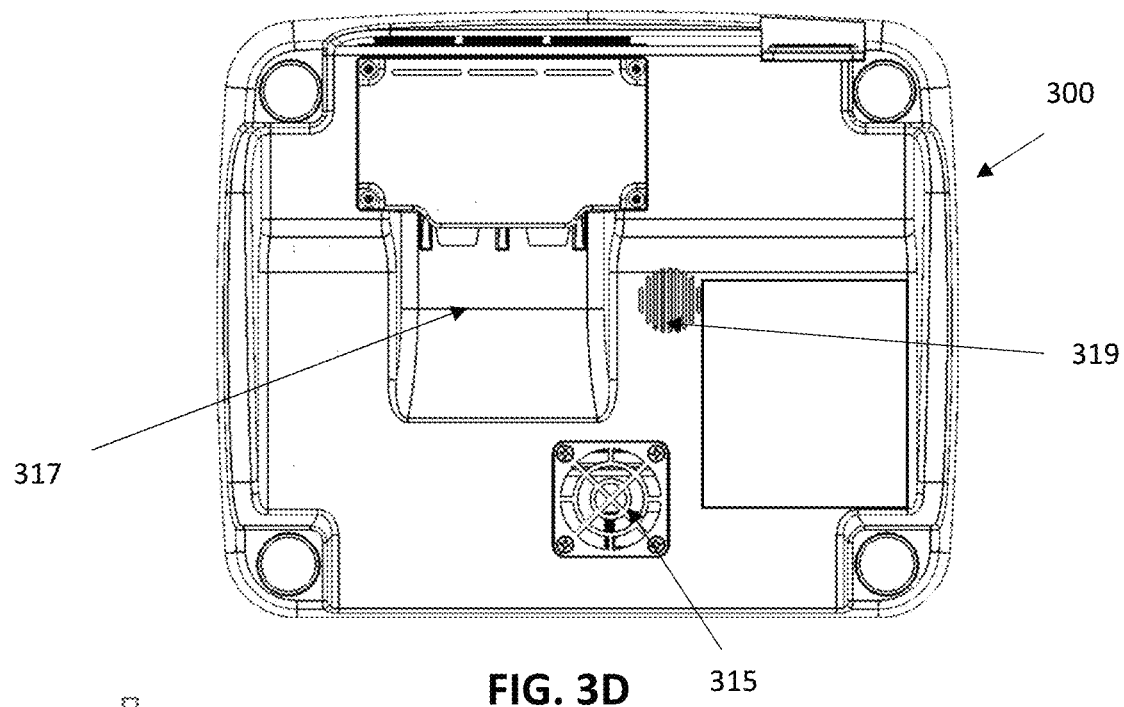

FIG. 3D shows a bottom view of the high-power pulsed electromagnetic field (PEMF) applicator apparatus, showing the cooling fan outlet 315, speaker outlet 319 and a cable management region 317 for coupling to and securing the cables connecting to the applicators (not shown).

Figure 4A:
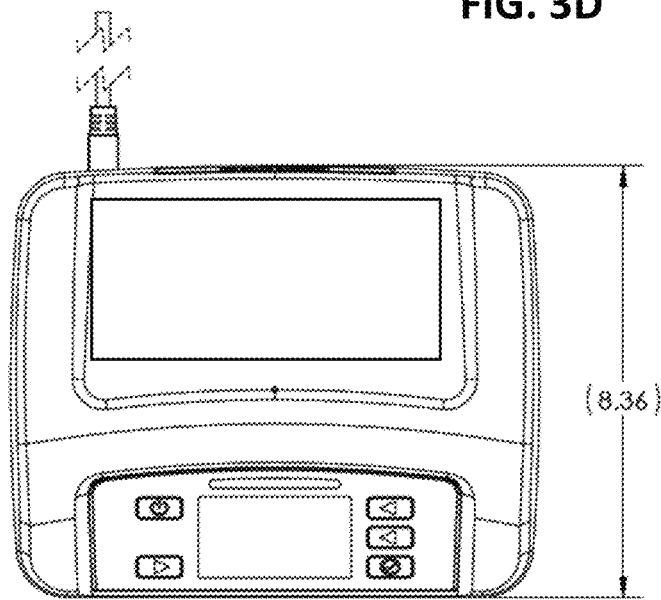
FIGS. 4A and 4B illustrate exemplary dimensions (in inches) for the base unit of FIG. 3A-3D.
Figure 4B:
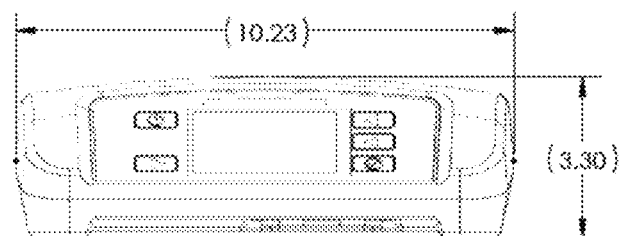

FIGS. 4A-4B illustrate exemplary dimensions for an apparatus similar to that shown in FIGS. 3A-3D. These dimensions (shown in inches) are exemplary only, and may be +/−50%, 40%, 30%, 25%, 20%, 15%, 10%, 5%, etc.

Figure 5:
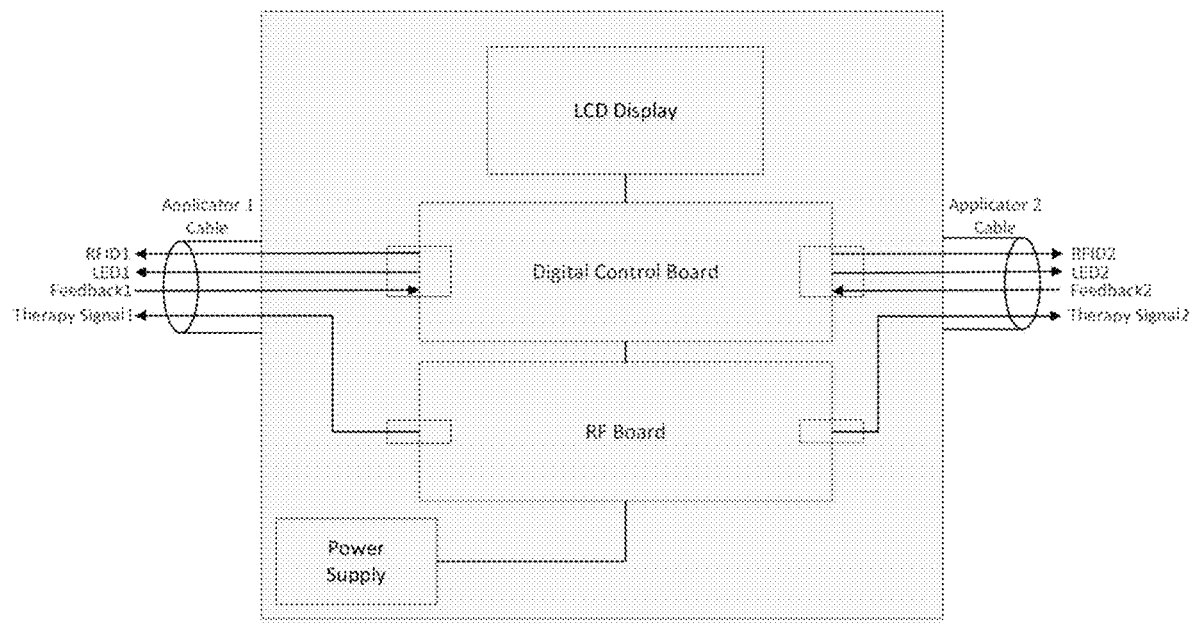
FIG. 5 schematically illustrates one example of a control circuit for a base unit for a high-power pulsed electromagnetic field (PEMF) applicator system.

FIG. 5 schematically illustrates an example of a block diagram of the base unit of a high-power pulsed electromagnetic field (PEMF) applicator apparatus. The block diagram includes a display (LCD display), a controller (including a digital control board), and an RF board, all of which may be connected to a power supply, which may include circuitry (power control circuitry) for providing the power both to operate the circuitry as well as to apply to the applicators. A pair of applicator cables (applicator cable 1 and applicator cable 2) are shown, which may connect to each of two applicators and may carry both power ("therapy signal 1" and "therapy signal 2") and data (e.g., RFID information 1, LED power, feedback from the applicator). The feedback may be, for example, field strength, etc.

Figure 6:
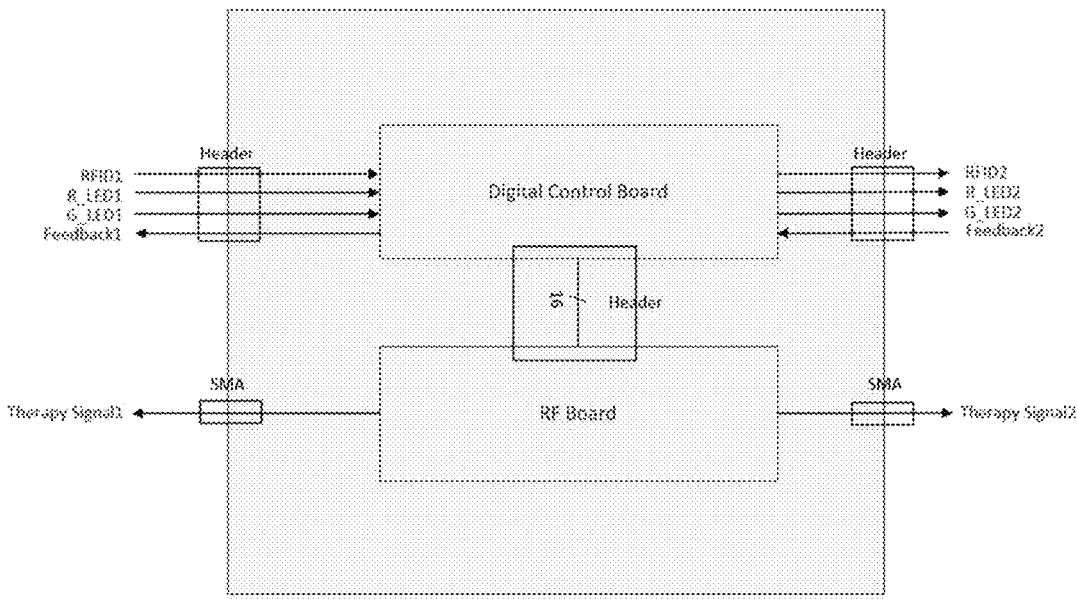
FIG. 6 schematically illustrates another example of a base unit for a high-power pulsed electromagnetic field (PEMF) applicator system, similar to that shown in FIG. 5.
Figure 7:
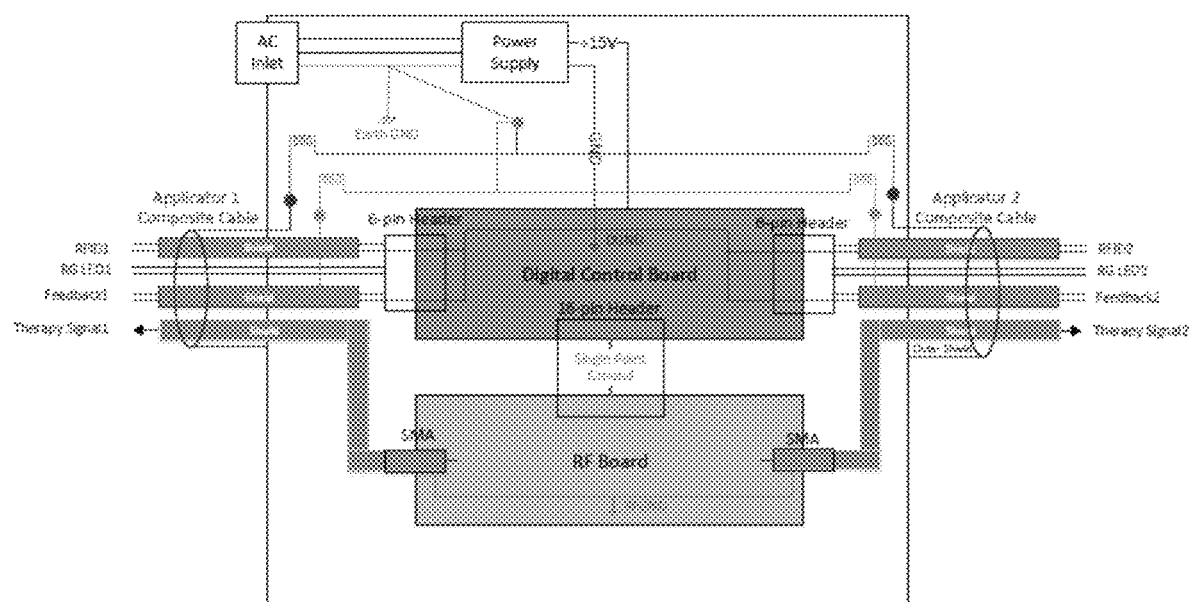
FIG. 7 schematically illustrates one example of a grounding diagram design for a high-power pulsed electromagnetic field (PEMF) applicator system.

FIG. 6 is another schematic of an applicator interface shown the signal processing between the digital control board, the applicators, and the RF board. Generally, data is transmitted to/from the digital control board (controller/processor) and power is applied as a signal (PEMF signal) to the applicator by the RF board. FIG. 7 shows a ground diagram for one example of a high-power pulsed electromagnetic field (PEMF) applicator apparatus. In this example the power supply, control circuity (digital control board), RF board and applicators are all grounded by the common ground form the AC inlet. All of the cables are shielded cables with the shields being grounded. Finally shielding in the applicator is also grounded to the same common ground.

Figure 8A:
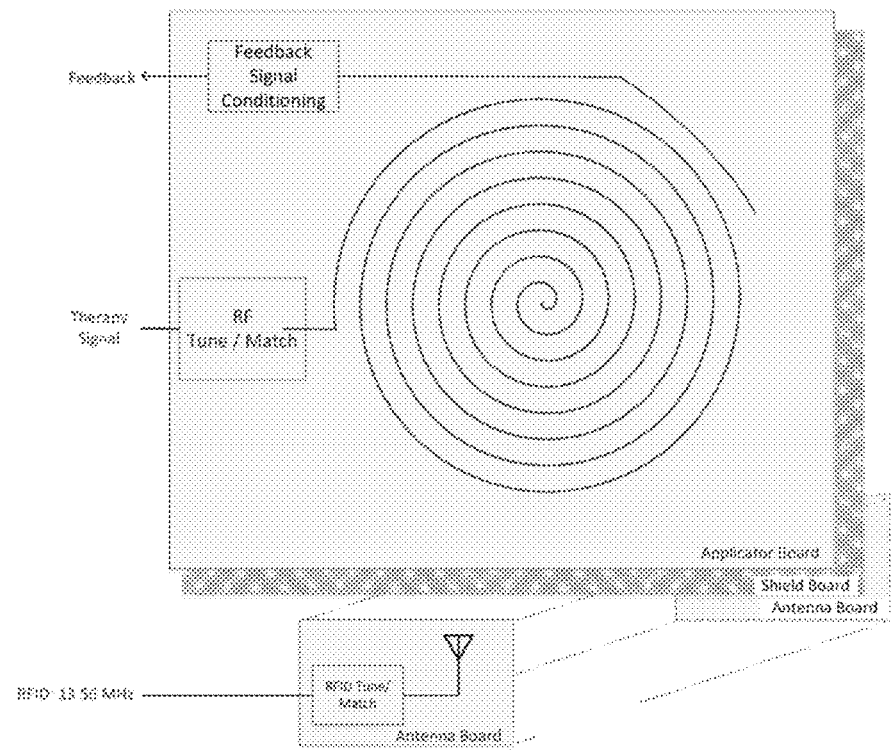
FIG. 8A schematically illustrates one example of an applicator for a high-power pulsed electromagnetic field (PEMF) applicator system.
Figure 8B:
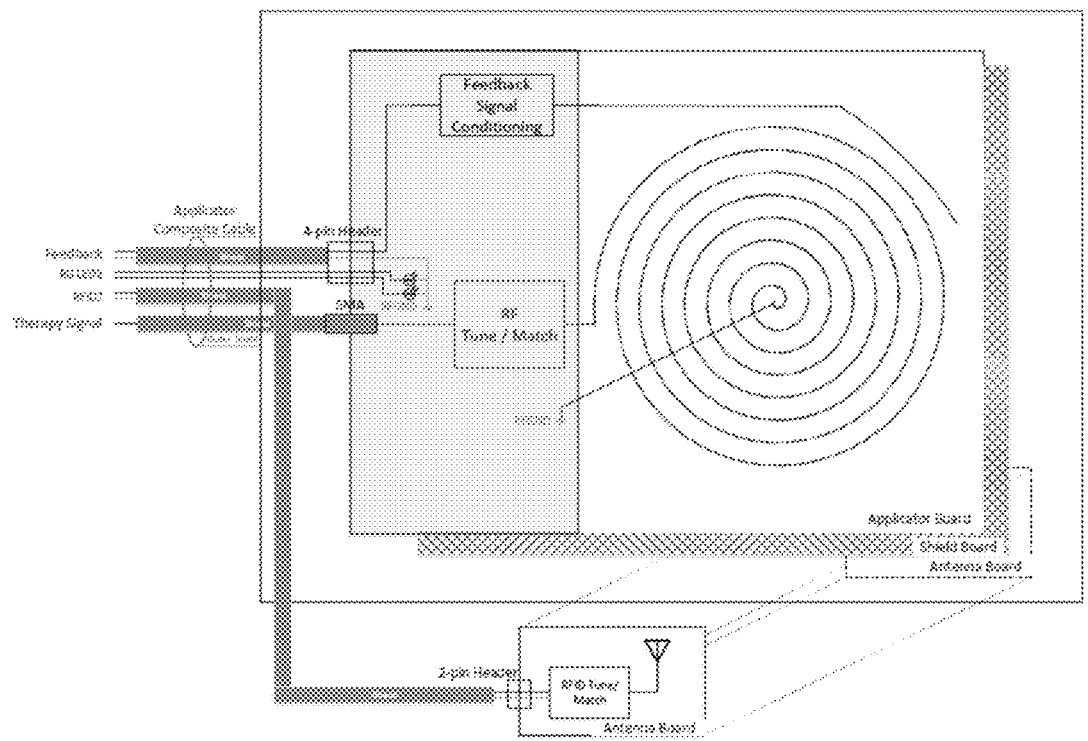
FIG. 8B is another schematic of the applicator of FIG. 8A, showing a grounding diagram with cabling connections, similar to FIG. 7.
Figure 8C:
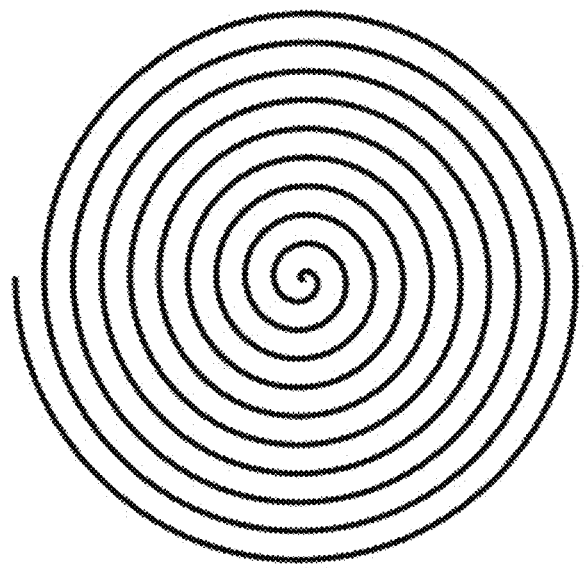
FIGS. 8C and 8D illustrate examples of applicator antenna coils that may be used.
Figure 8D:
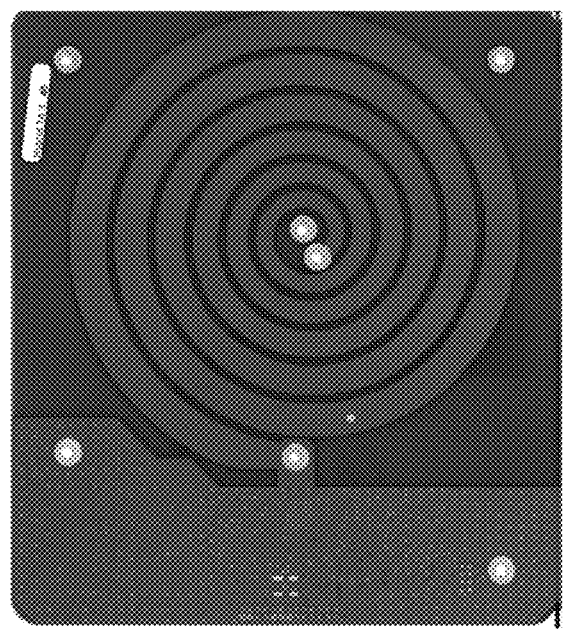

FIGS. 8A-8B schematically illustrate applicators for one example of a high-power pulsed electromagnetic field (PEMF) applicator apparatus. In this example, the apparatus includes an antenna for delivery of the high-energy PEMF energy. The antenna may be a coil, such as shown in either FIG. 8C or 8D. The applicator may also include a feedback signal sensor ("feedback signal conditioning") that may be used in a closed-loop manner to adjust the applied energy, including detecting field strength and/or load. The schematics in FIGS. 8A and 8B also shown the applicator board on which the antenna is positioned. A shielding board is positioned behind the applicator board and a separate antenna board, which may include an RFID tuner may be located on the separate applicator board.

Figure 9B:
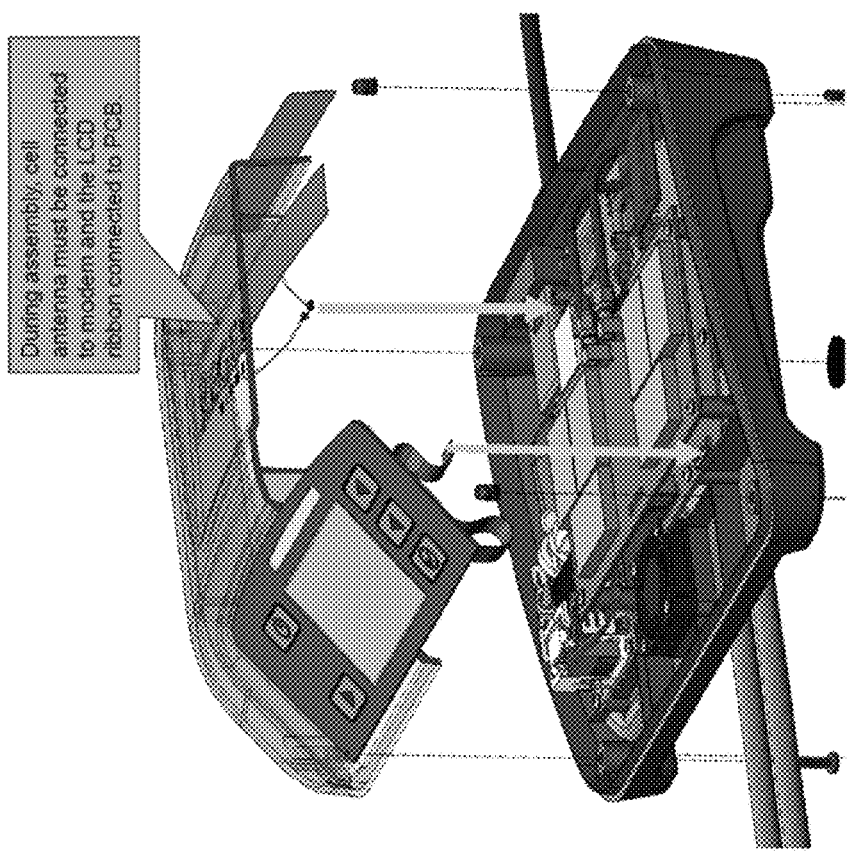
FIGS. 9A and 9B illustrate an example of exploded views of a base unit for a high-power pulsed electromagnetic field (PEMF) applicator system, showing the arrangement of components in one example.
Figure 9A:
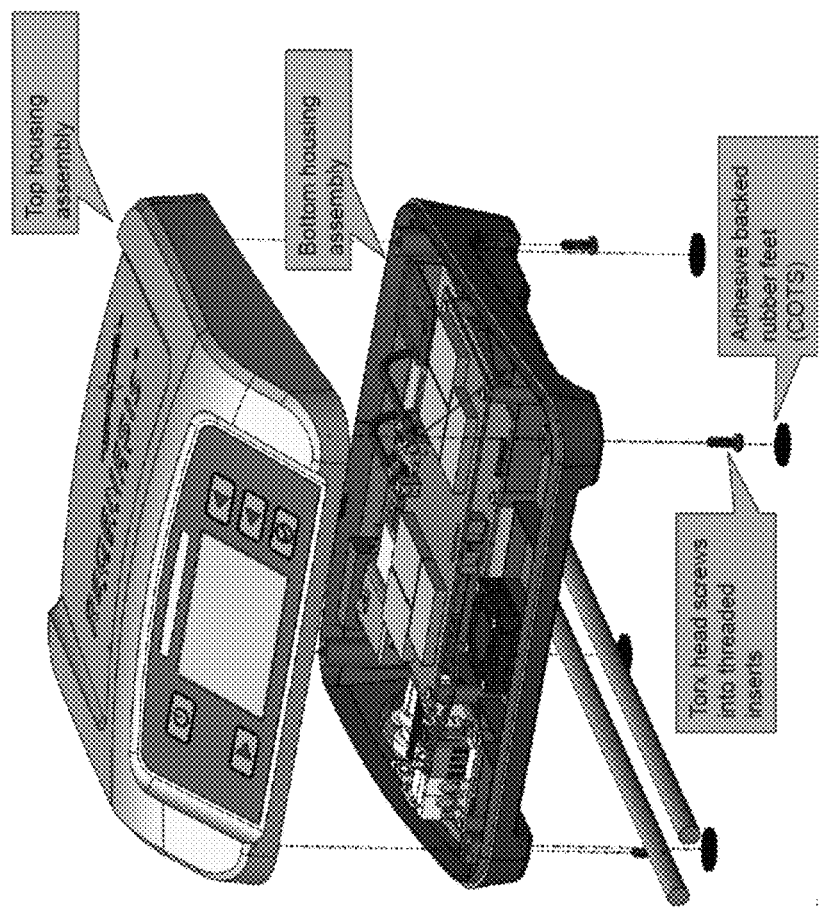

FIGS. 9A-16B illustrate various views of the base unit of a high-power pulsed electromagnetic field (PEMF) applicator apparatus. For example, FIGS. 9A-9B show a view of the internal organization of a base unit with the top housing assembly separated from the base housing assembly. The notes on these figures highlight features of the apparatus. For example, FIG. 10A shows one example of a display panel (membrane panel) that may be used.

Figures 10A, 10B:
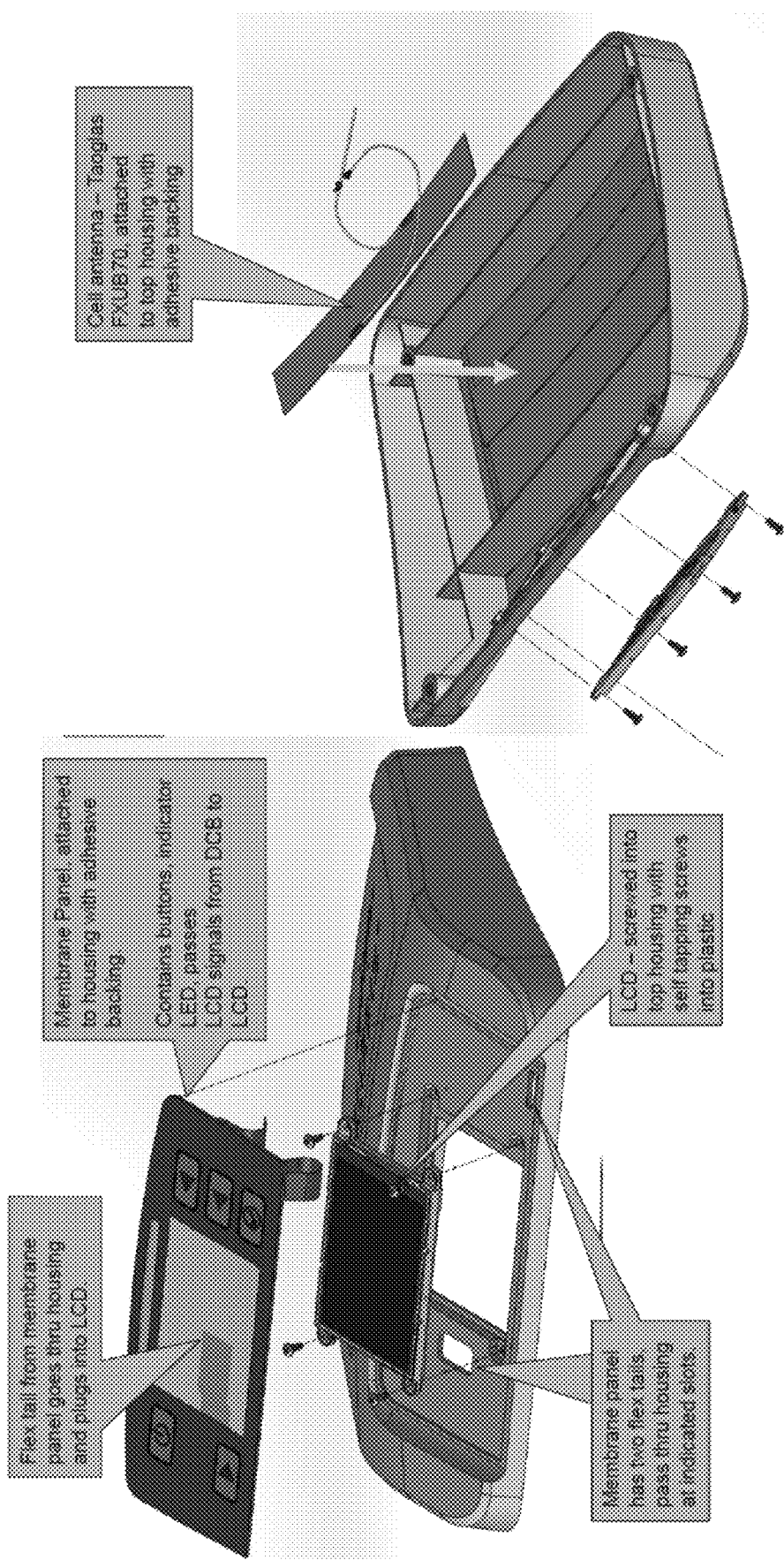
FIGS. 10A-10B illustrate one example of a display/user interface and wireless antenna for a high-power pulsed electromagnetic field (PEMF) applicator system.

FIG. 10B show the attachment of a cellular antenna that may be included within the housing (or on top of the housing) for connection to the communications circuitry, as described above.

Figure 11:
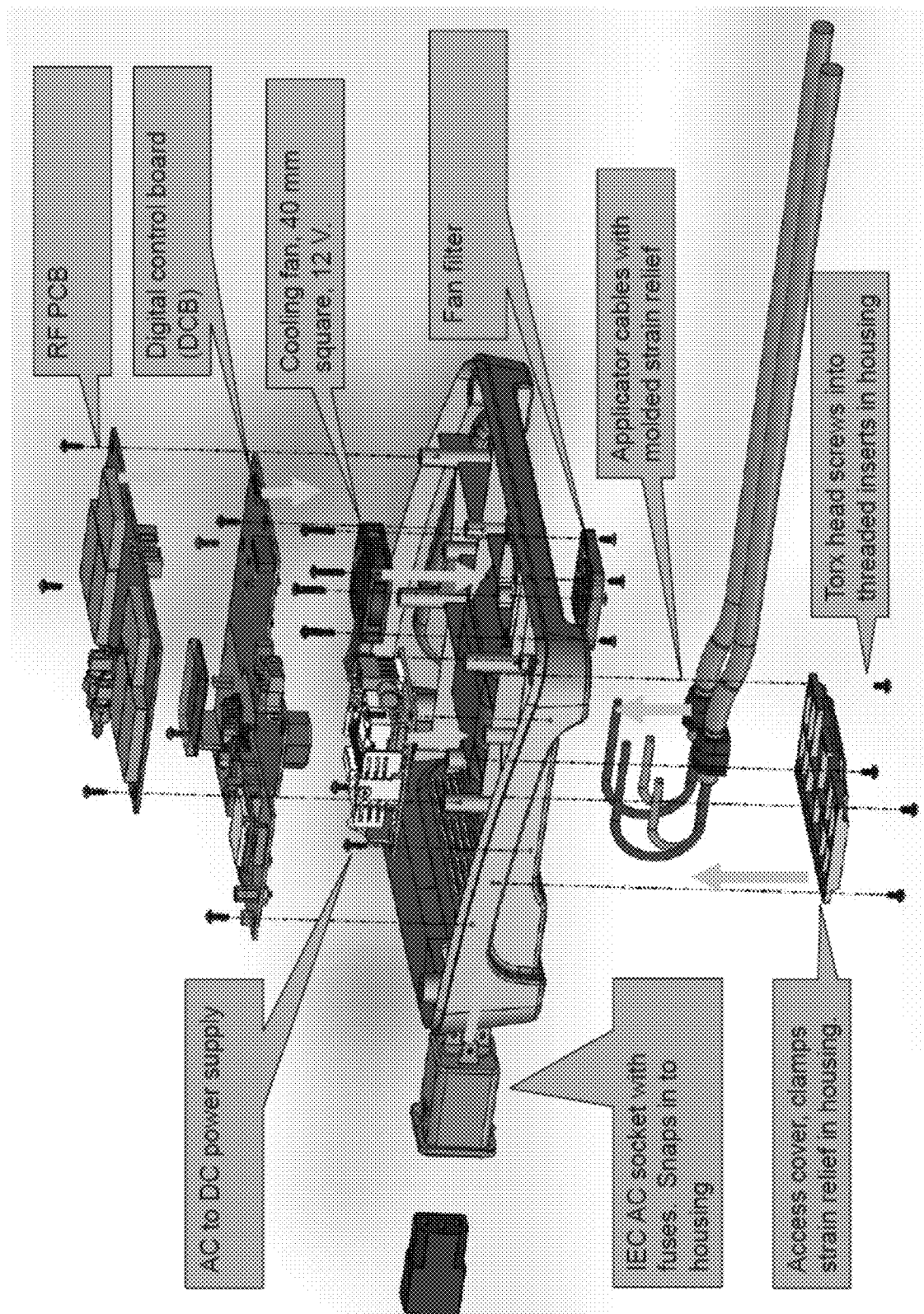
FIG. 11 shows a detailed exploded view of a base unit of an exemplary high-power pulsed electromagnetic field (PEMF) applicator system similar to that shown in FIGS. 1 and 2.
Figures 12, 13:
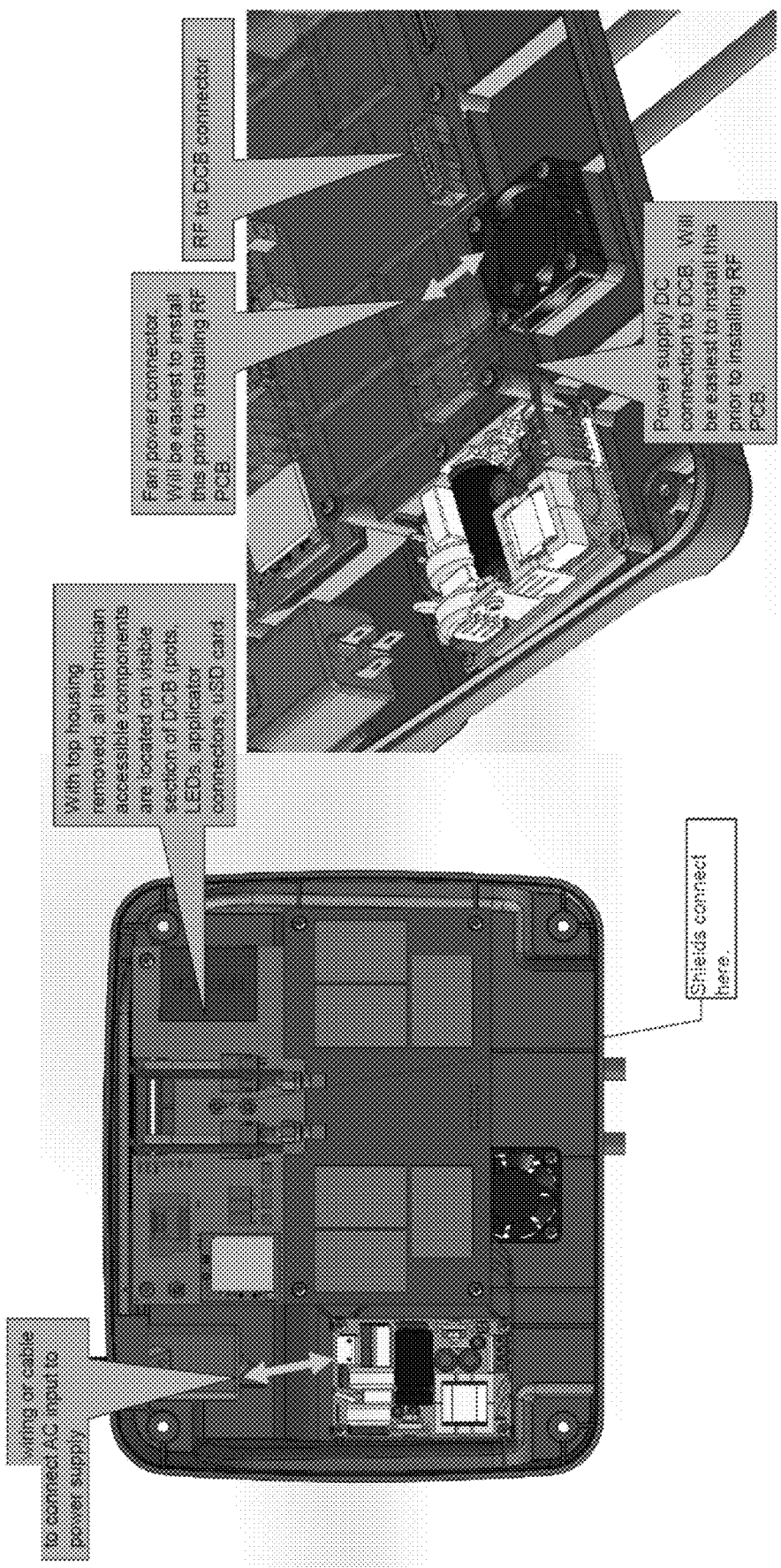
FIG. 12 is an example of a top view down into the bottom portion of a base unit of a high-power pulsed electromagnetic field (PEMF) applicator system showing cabling components and cooling sub-systems.
FIG. 13 is an example of an internal portion of a base unit such as the one shown in FIG. 12.

An exploded view of an exemplary high-power pulsed electromagnetic field (PEMF) applicator apparatus is shown in FIG. 11, showing an arrangement of the RF PCB (driving the application stimuli of the one or more applicators), digital control board (DCB or controller), cooling fan and fan filter, and AC/DC power supply. The cables and an access cover are also shown. FIG. 12 is an example of a bottom of the inside of the housing assembly, and FIG. 13 shows the location of the power supply and cooling fan, in one example. FIGS. 14A-14B illustrate the bottom outside of the housing of the base unit, showing the fan intake and cable connector as well as fan exhaust slots on the back side of the apparatus.

The arrangement of the components within the base unit housing may be configured both to maximally shield the components from the RF fields produced by some of them and to enhance cooling and air circulation. As shown in FIG. 12, one or more RF shield cans (shown in grey) may cover the RF amplification stages, and may be positioned on one side of an RF board (RF PCB). A separate digital board may hold other elements of the device, including the controller circuitry (processor, clock, memory, etc.). The digital board and certain of the components may be sensitive to the RF radiation. In some variations, the digital board and the RF board may be separated by an air gap and face away from each other, so that the RF amplification stages (covered by the additional shielding (cans) may be on a side of the RF board, which may also include shielding, facing away from the more RF-sensitive digital board, on which other components are located; the RF-sensitive components on the digital board (digital PCB board) may be positioned on a side of the digital board that is opposite from the RF board. Furthermore, as shown, the RF board and the digital board may be staggered relative to each other so that they do not align (e.g. they are laterally offset). The power RF elements are on one side of the RF board, and may be positioned on a non-overlapping end region of the board; on the digital board, any element having an inductive component (or that is otherwise sensitive to the high RF fields generated) may be positioned on the non-overlapping end of the digital board. This arrangement, in addition to the RF shielding on each PCB, may maximally prevent interference between the two. Thus, the components may be on opposite sides of the boards, each board may include a ground plate, and there may be an air gap between the two plates. Further, the boards may be laterally offset.

As shown in FIGS. 12-15C, as a consequence of this, the cables may be inserted into the bottom of the device and brought up through the digital board and feed back to the SMA connectors. The routing of the cables within the device may be arranged to minimize the antenna effects that they may otherwise cause. Further detail is provided in the grounding diagrams, including FIGS. 7 and 8B, discussed above.

FIGS. 15A-15C illustrate the applicator cable installation into the base unit.

Figures 16A, 16B:
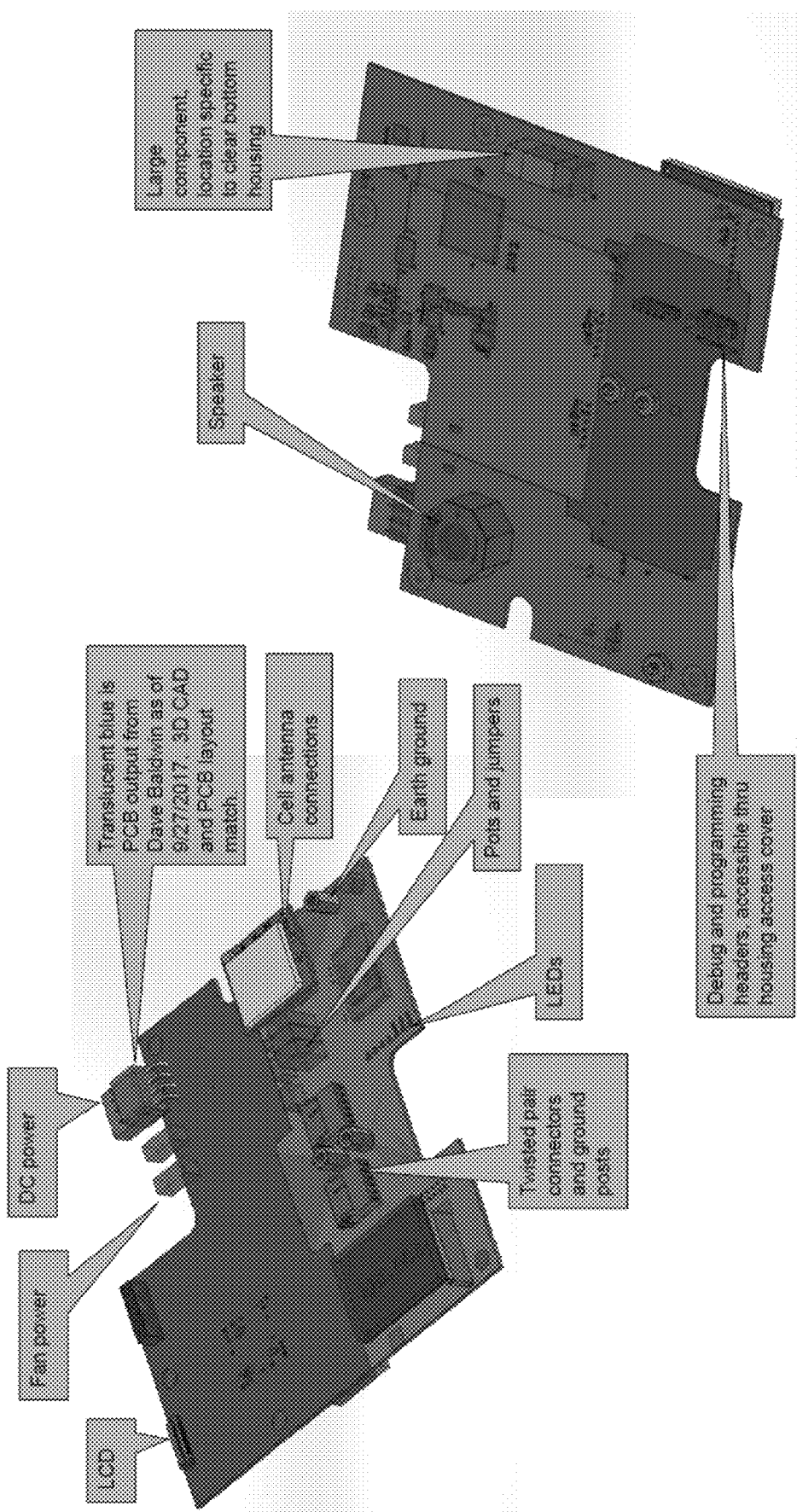
FIGS. 16A-16B schematically illustrate top and bottom views, respectively of an exemplary digital control board (DCB) for a high-power pulsed electromagnetic field (PEMF) applicator system base unit.
Figure 17:
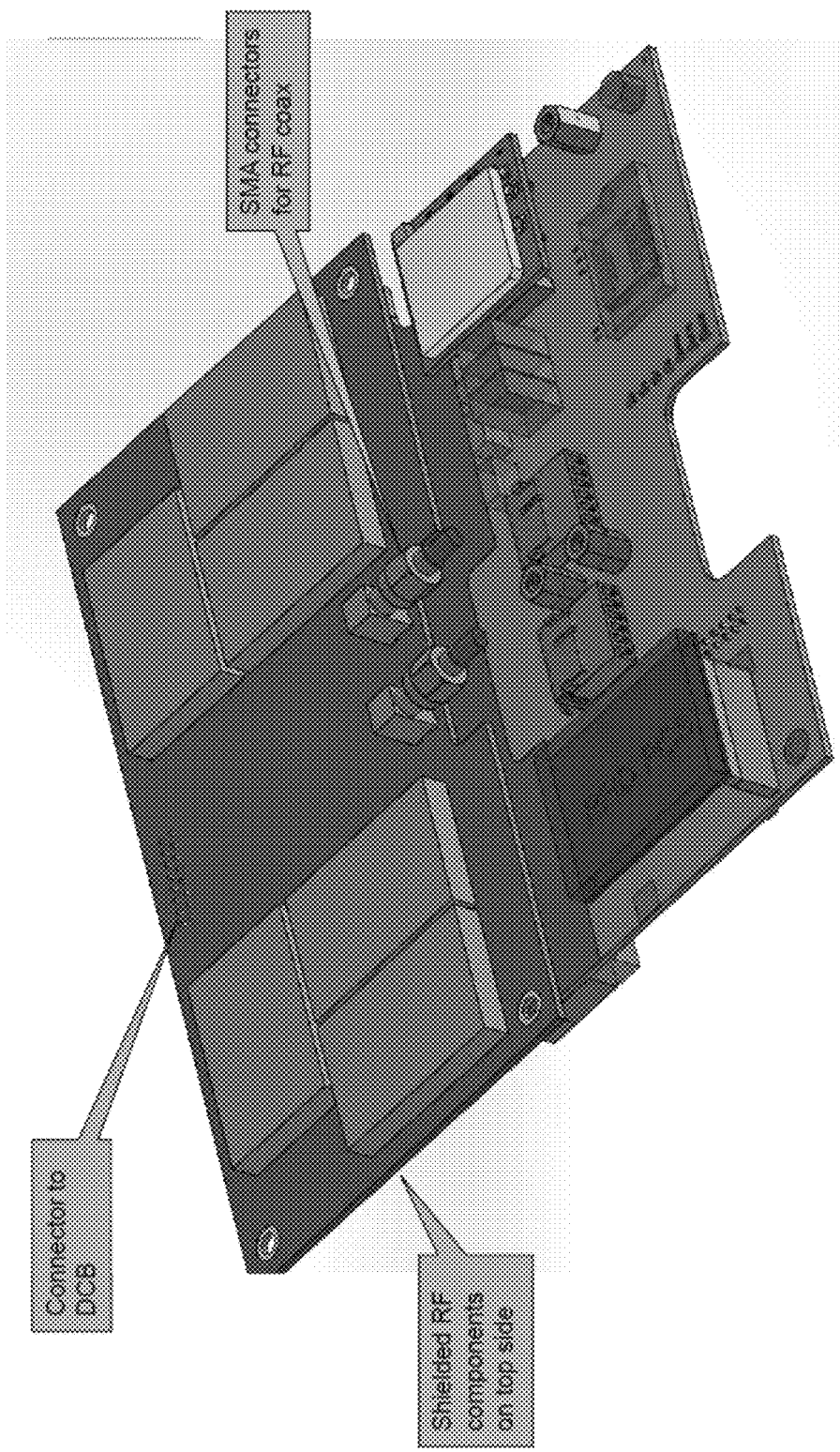
FIG. 17 schematically illustrates a top view of a radio frequency (RF) PCB for a high-power pulsed electromagnetic field (PEMF) applicator system base unit.

FIGS. 16A-16B illustrate examples of the circuit boards within the base unit. In FIGS. 16A-16B an example of one variation of a DCB (digital control board) is shown with the various components indicated. This board may function as the controller and may include a processor, memory, clock, etc. and may coordinate the activity of the other components.

An example of an RF printed circuit board, which may prepare the RF (e.g., PEMF) signals for application by the applicators. The RF components may be on a side that is shielded from the other circuitry and opposite to the controller circuitry.

Figure 18:
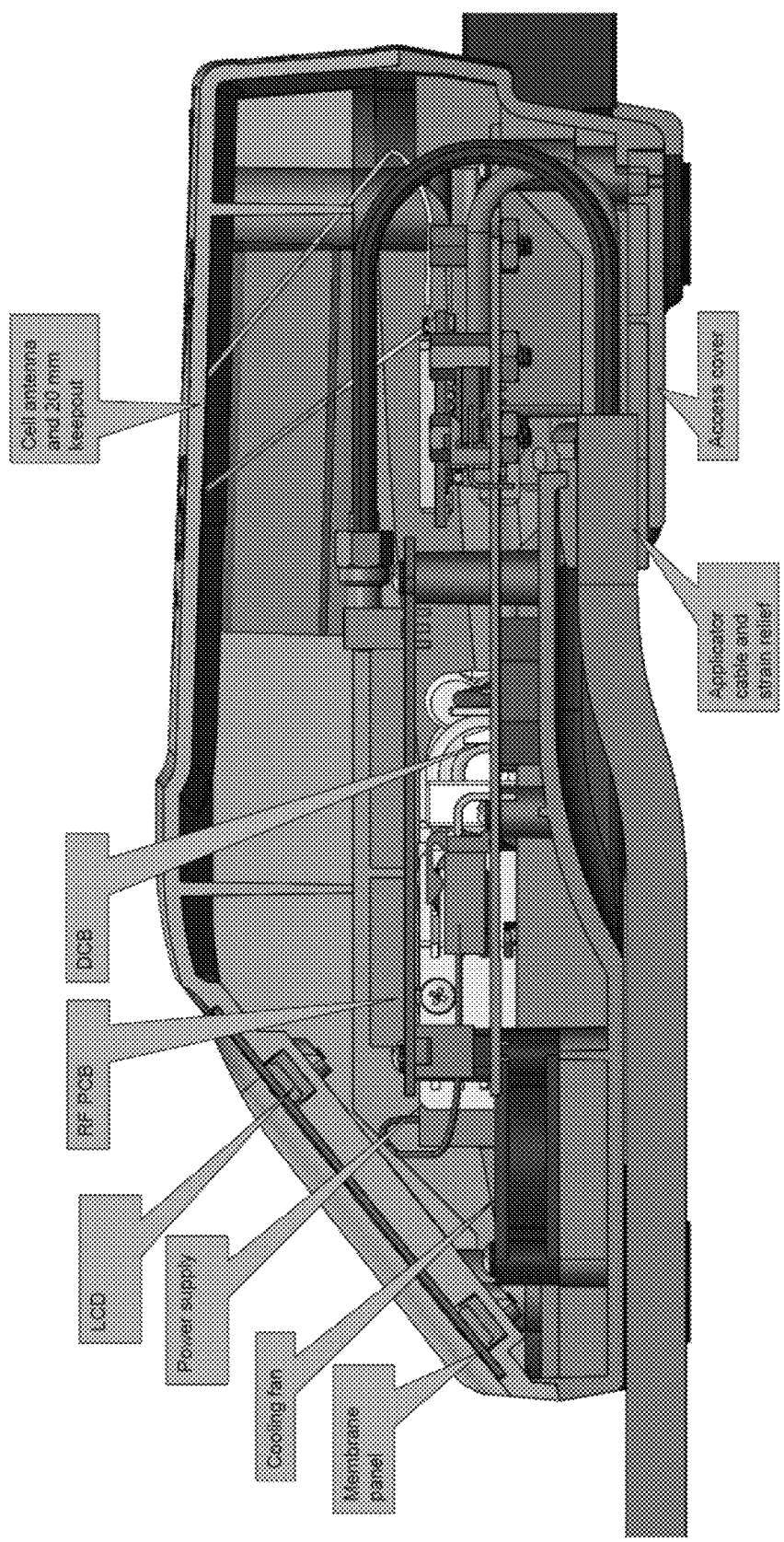
FIG. 18 is an exemplary cross-section through a base unit of a high-power pulsed electromagnetic field (PEMF) applicator system.

The cross-section shown in FIG. 18 illustrates one example of an arrangement of these components within the base unit housing. The internal features of the housing may include one or more ribs, projections, etc. to hold the components in place. These internal structures may also help regulate airflow from the cooling fan, as described in reference to FIGS. 20A and 20B.

Figure 20A:
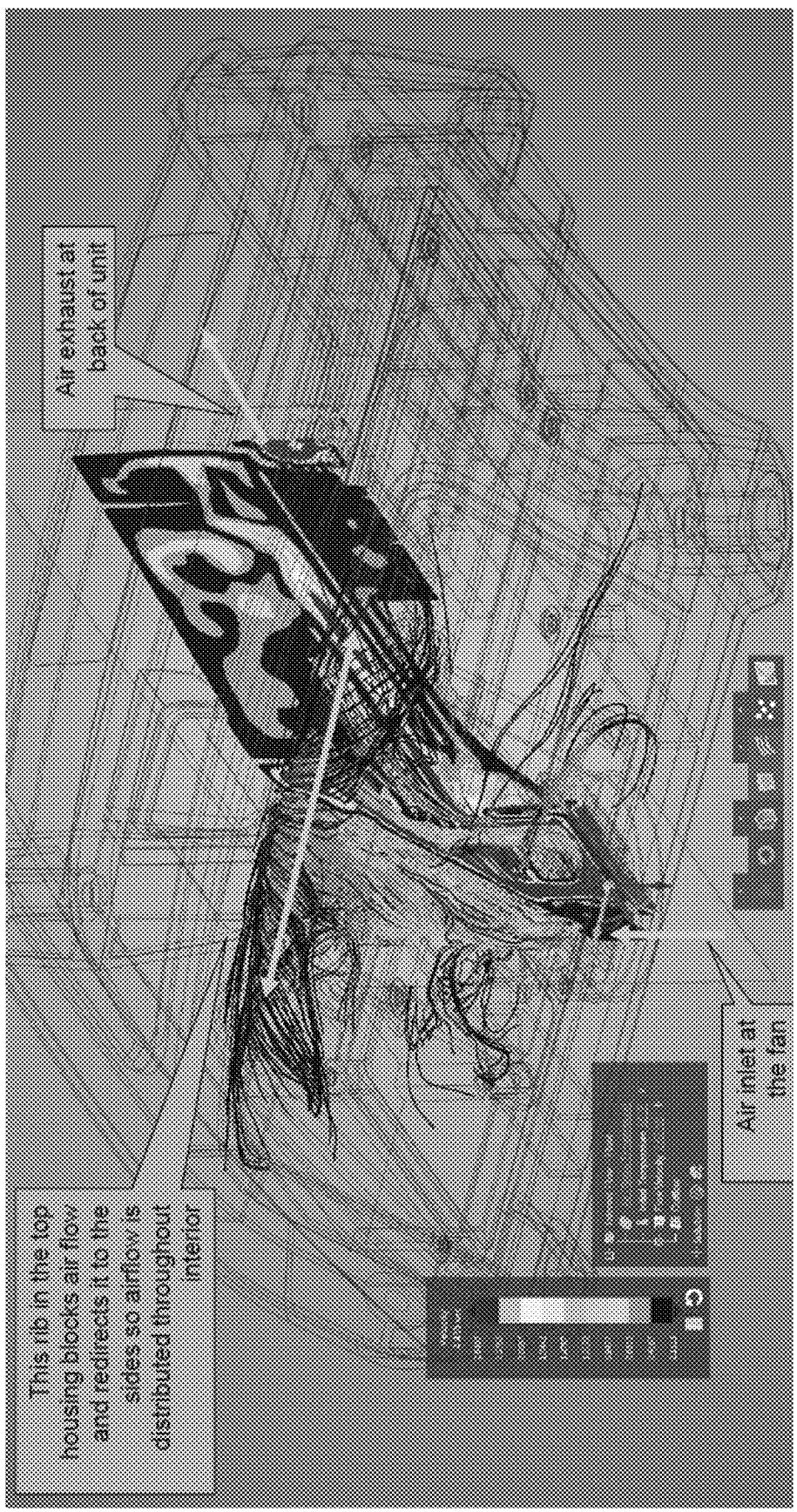
FIGS. 20A and 20B illustrate simulated cooling airflow profiles for a high-power pulsed electromagnetic field (PEMF) applicator system configured as described herein. As described herein the internal components within the housing may be configured to avoid both excessive heat (allowing airflow as shown) and also to avoid inductive coupling between the various electronic components, including those (such as the RF amplifier stages) that produce large fields.
Figure 20B:
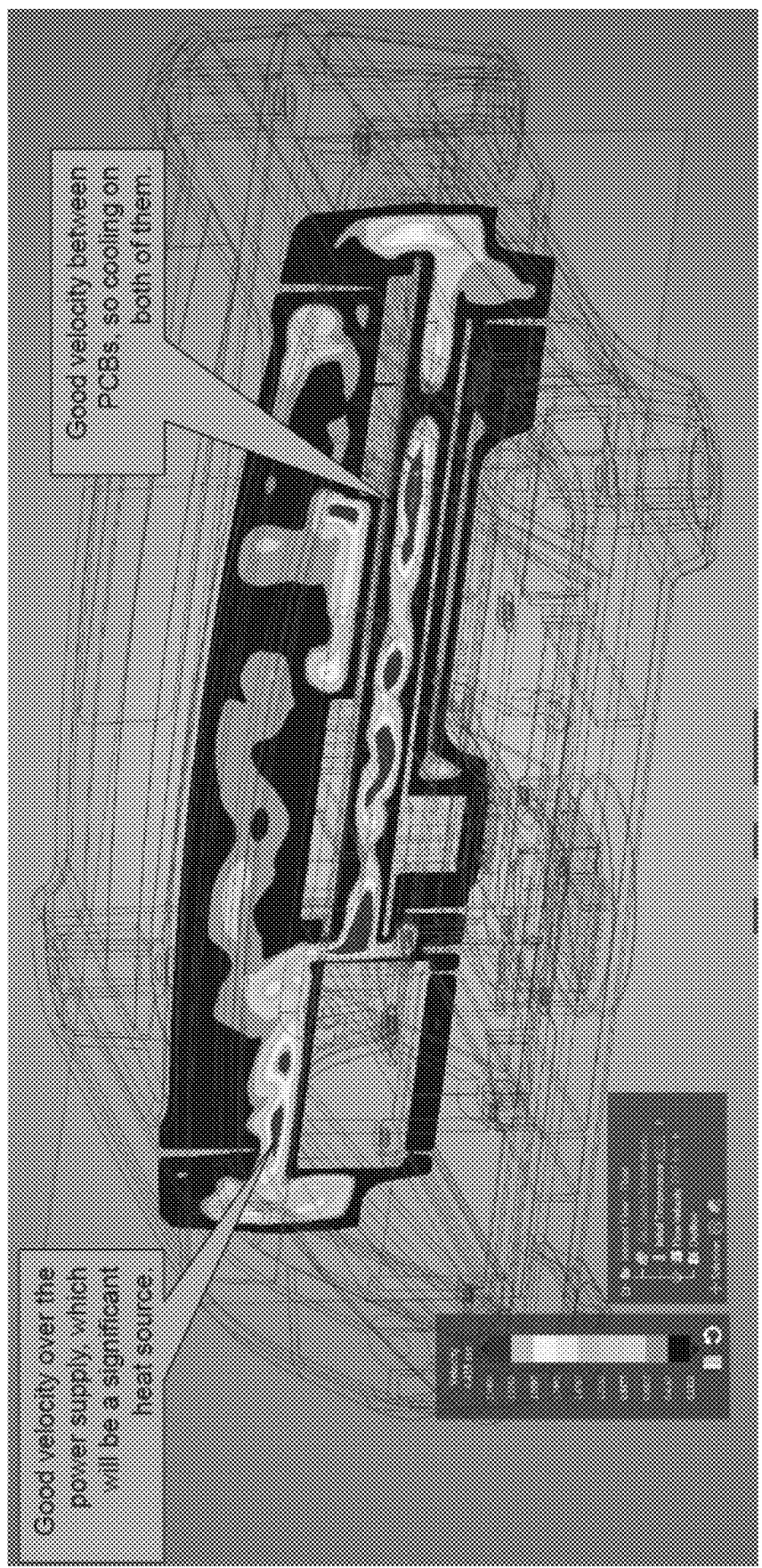

In FIG. 20A, a heat map shows the relative flow of air through the housing from the fan, when operating in normal conditions. In this model, the airflow starts from the fan at the front of the base unit, and travels around the interior in a pathway defined in part by the ribs within the housing unit, so that the air is channeled around the heat-generating components at relatively high flow rates (e.g., between 0.4 and 5 ft/sec). In FIG. 20A, the upper rib spanning the length of the top of the housing helps redirect the air over the circuitry and power supply. Air generally flows in from the front bottom (fan inlet) and out through the back outlet. The controller PCB and the RF PCB are separated by an air gap through which airflow is directed, as shown in FIG. 20B.

Any of these apparatuses may be configured to avoid water damage. For example, FIGS. 19A-19B illustrate features that may be included to increase water resistance of the apparatus. In FIG. 19A, the slightly enlarged (compared to the lower housing cover) upper housing cover may prevent water from entering the housing. In this example, all of the opening into and out of the base unit are on the bottom, with the exception of the fan vents, which are protected by an overhang from the housing.

Figure 21A:
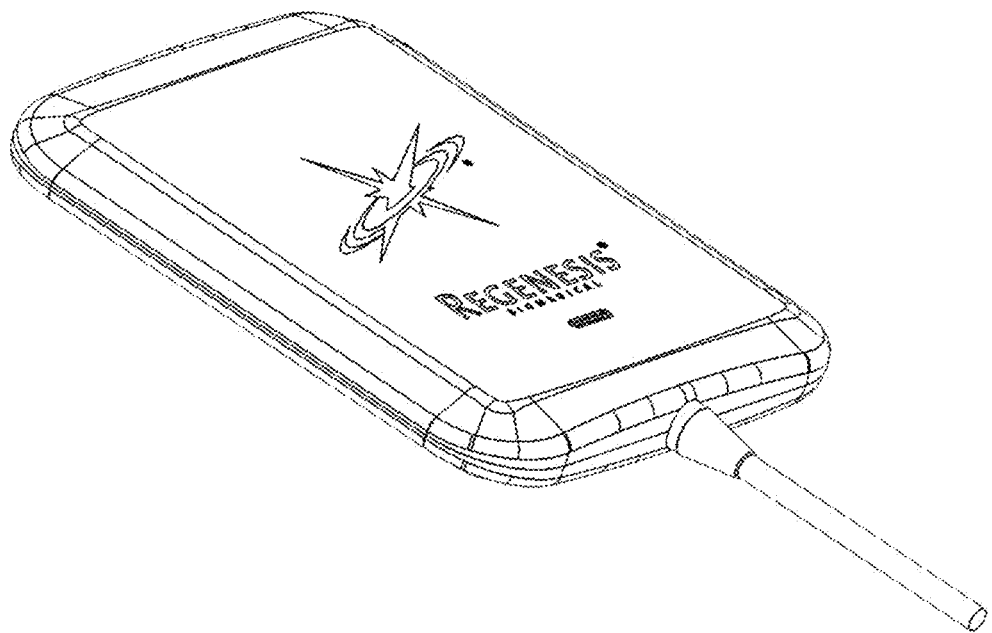
FIGS. 21A-21B illustrate top perspective and bottom perspective views, respectively, of an applicator for a high-power pulsed electromagnetic field (PEMF) applicator system as described herein.
Figure 21B:
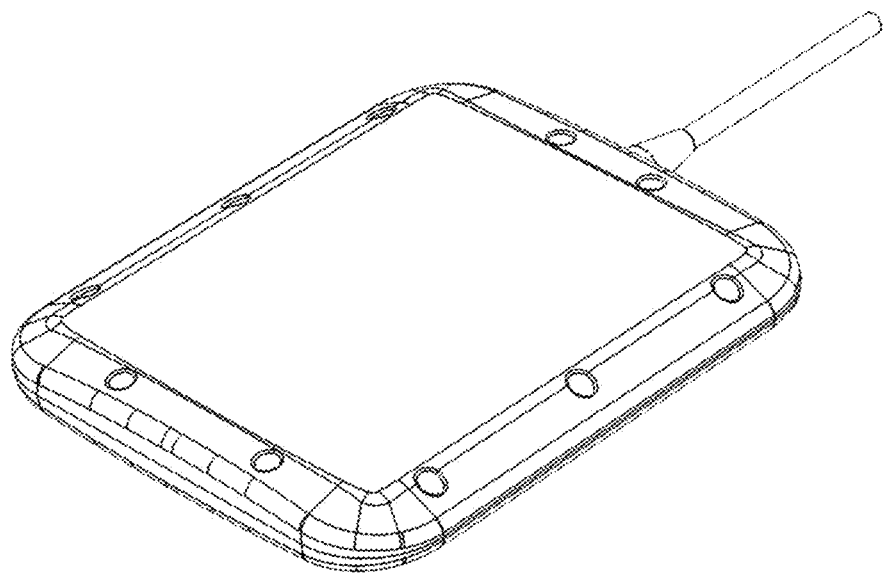
Figure 22A:
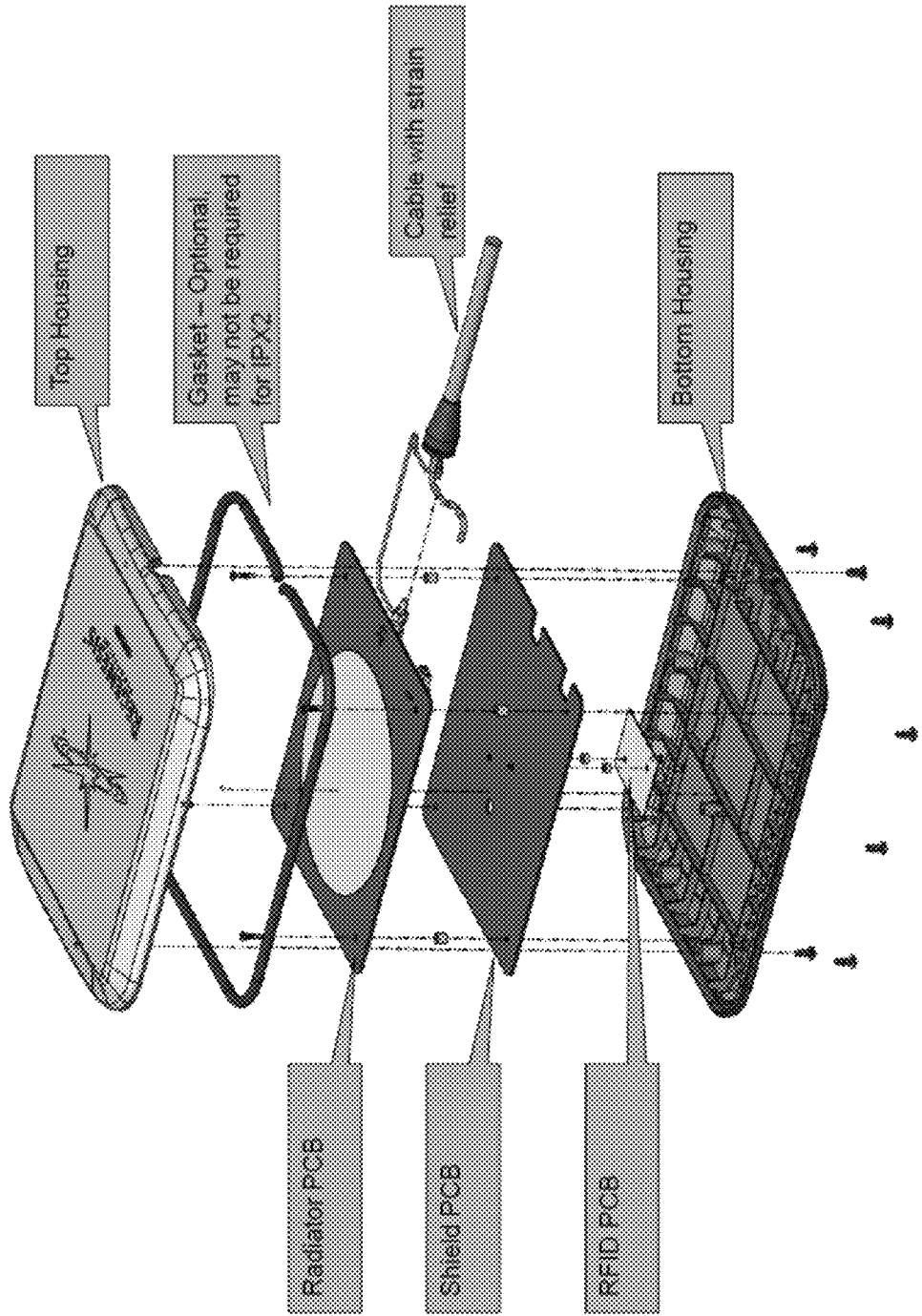
FIG. 22A shows a first exploded view of an applicator of a high-power pulsed electromagnetic field (PEMF) applicator system, similar to the one shown in FIGS. 21A-21B.
Figure 22B:
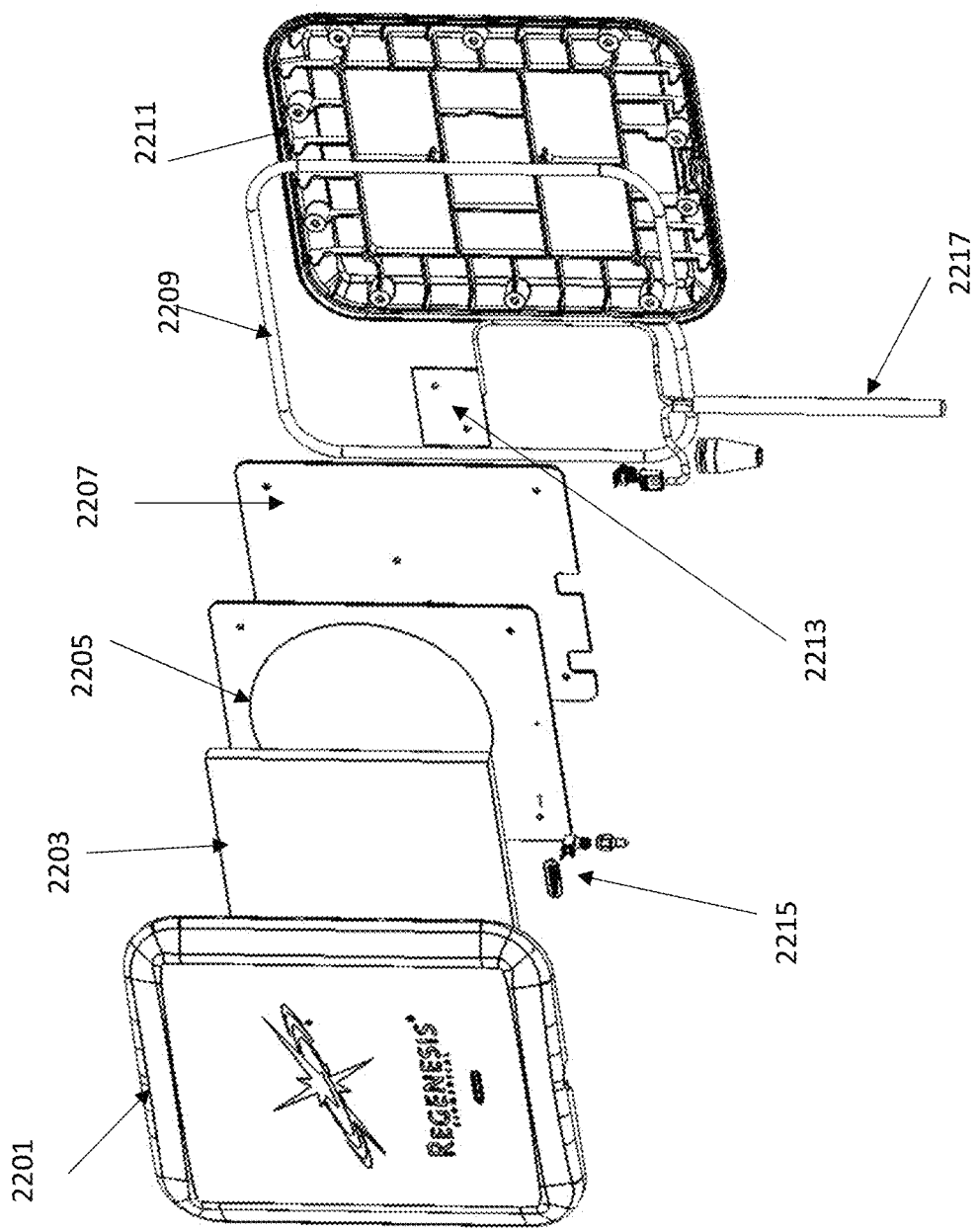
FIG. 22B is a second exploded view of an applicator of a high-power pulsed electromagnetic field (PEMF) applicator system as described herein.
Figure 23B:
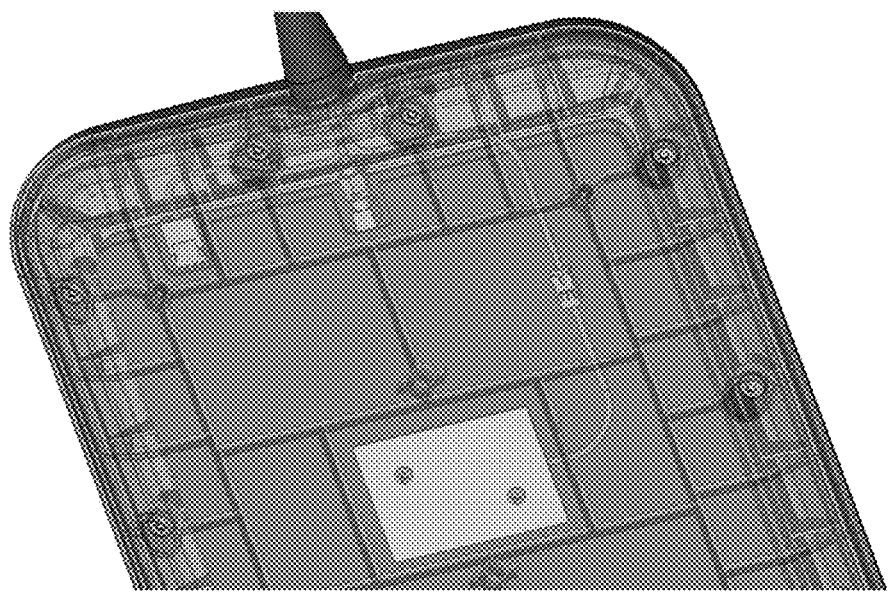
FIGS. 23A and 23B illustrate partially transparent views through alternative variations of an applicator such as the one shown in FIGS. 21A-21B.
Figure 23A:
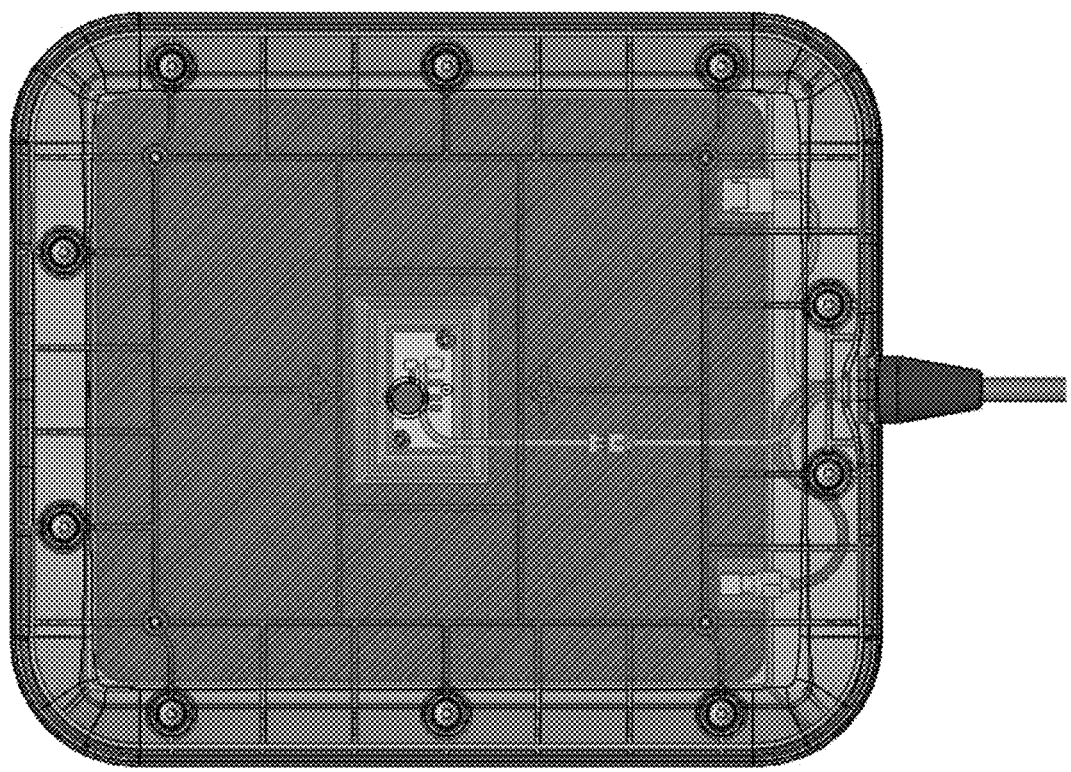
Figure 24A:
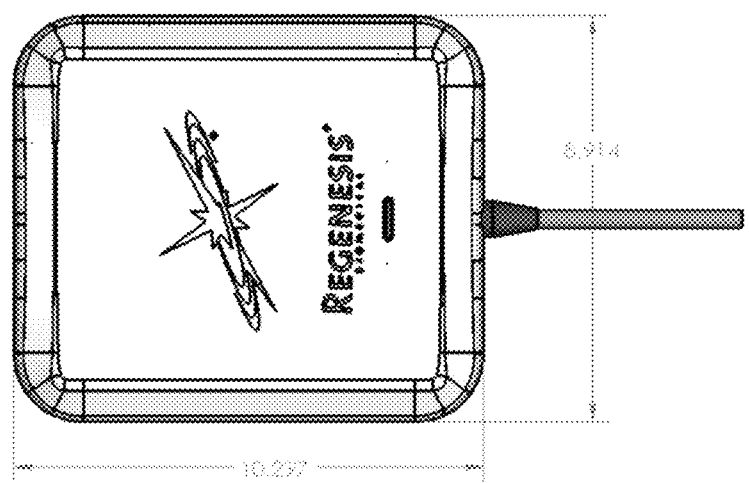
FIGS. 24A-24C show exemplary dimensions (in inches) for an applicator of a high-power pulsed electromagnetic field (PEMF) applicator system.
Figure 24B:
Figure 24C:
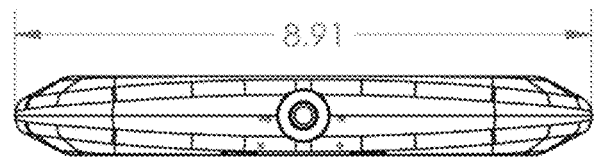

FIGS. 21A and 21B show schematic illustrations of an applicator that may be used with the high-power pulsed electromagnetic field (PEMF) applicator apparatuses described herein. In this example, the applicator is a rectangular, flat piece. FIG. 22A shows a first exploded view and FIG. 22B shows an alternative exploded view, showing the top housing 2201, a padding (e.g., neoprene) 2203, a radiator (e.g., PEMF antenna) PCB 2205, a shield PCB 2207, a gasket 2209, a bottom housing 2211, a cable 2217 connecting to the radiator PCB and the sensor and in some variations an RFID antenna 2213, as well as an LED light (e.g., light pipe 2215). FIGS. 23A and 23B show alternative applicators in which the bottom cover has been made transparent to show internal features.

Figures 27, 28:
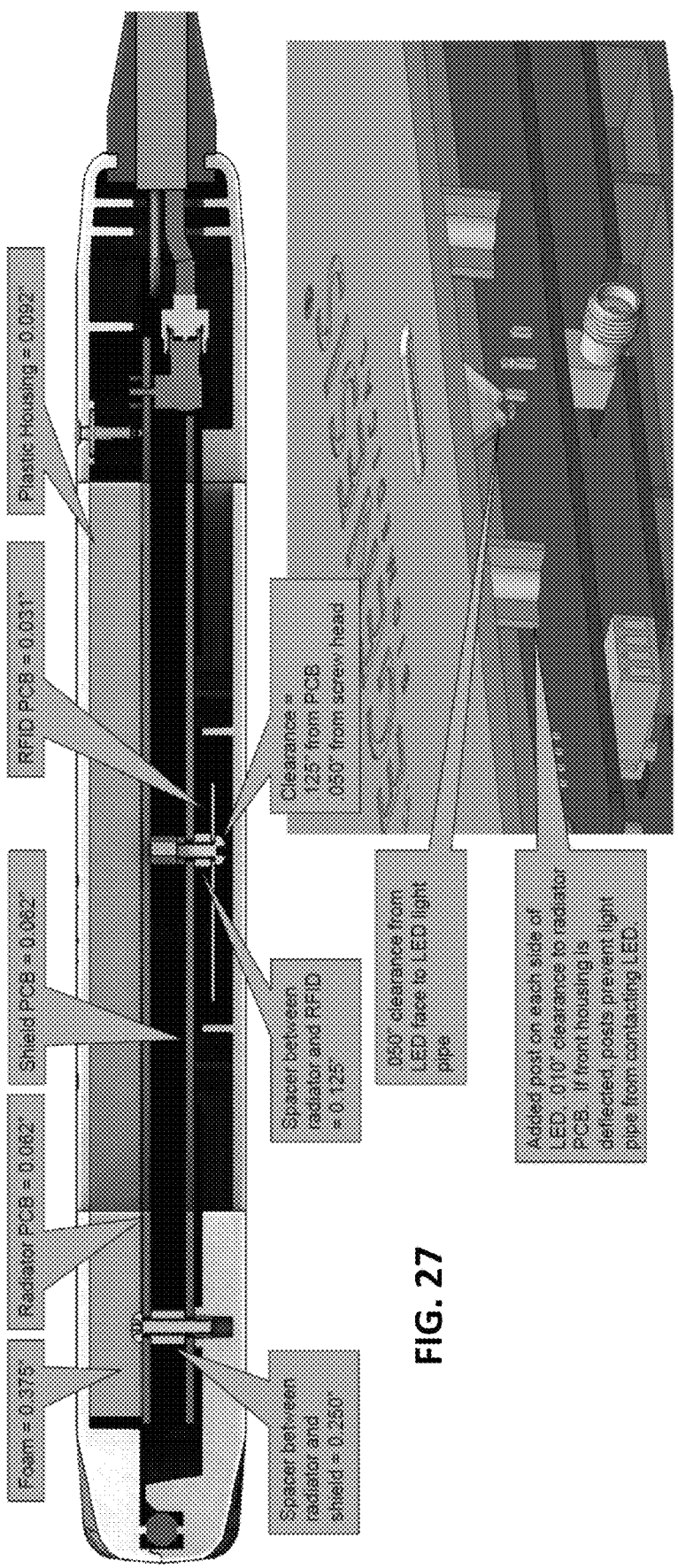
FIG. 27 illustrates a sectional view through an example of an applicator of a high-power pulsed electromagnetic field (PEMF) applicator system, showing exemplary dimensions (e.g., thicknesses) and clearances.
FIG. 28 is an example of a section through an applicator including an LED indicator (light pipe).

FIGS. 24A-24C and FIGS. 27-28 illustrate exemplary dimensions for one variation of an applicator. These dimensions (shown in inches) are exemplary only, and may be +/−50%, 40%, 30%, 25%, 20%, 15%, 10%, 5%, etc. In FIGS. 27-28, exemplary clearances are shown.

Figures 25A, 25B:
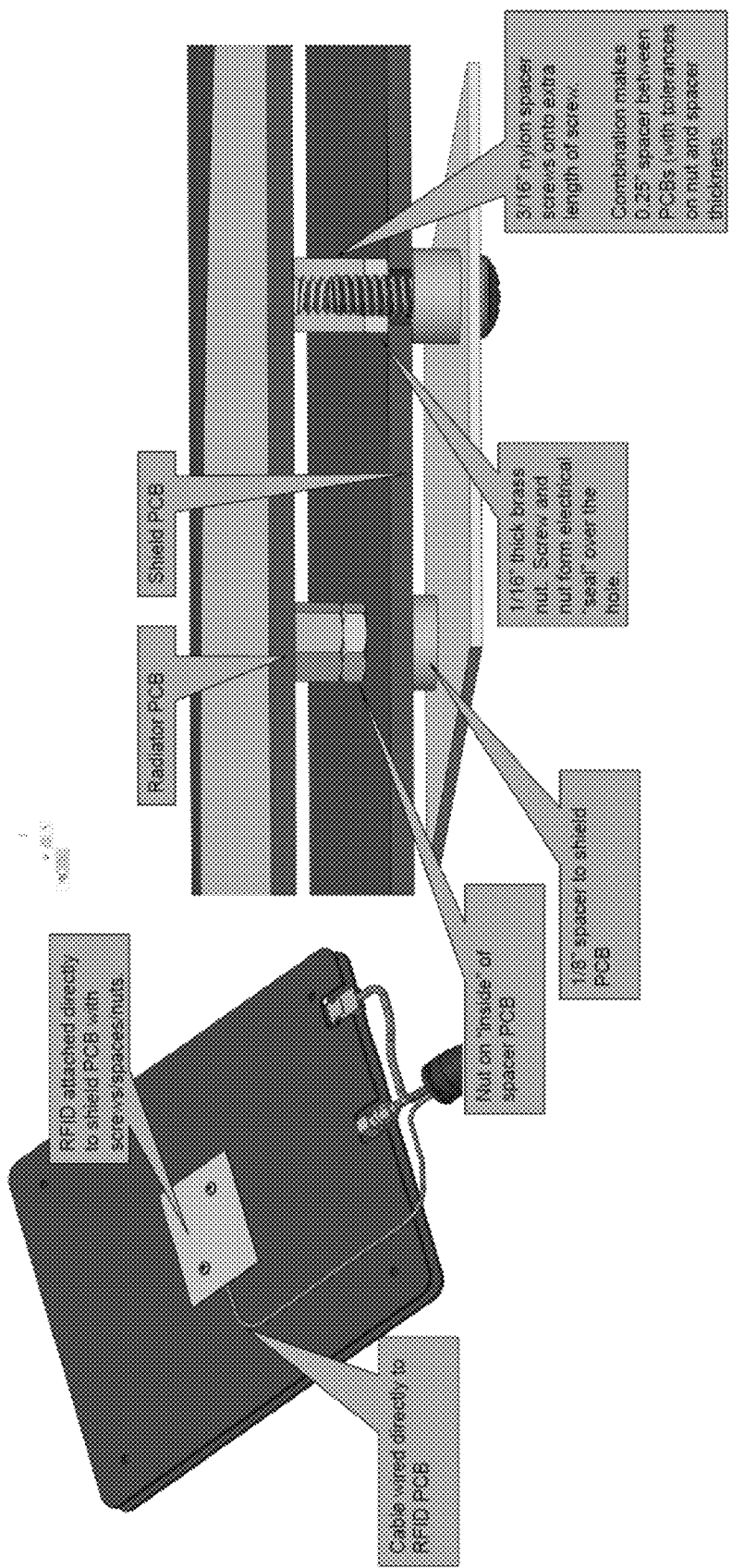
FIGS. 25A-25B illustrate examples of an RFID assembly of an applicator for a high-power pulsed electromagnetic field (PEMF) applicator system.
Figure 26E:
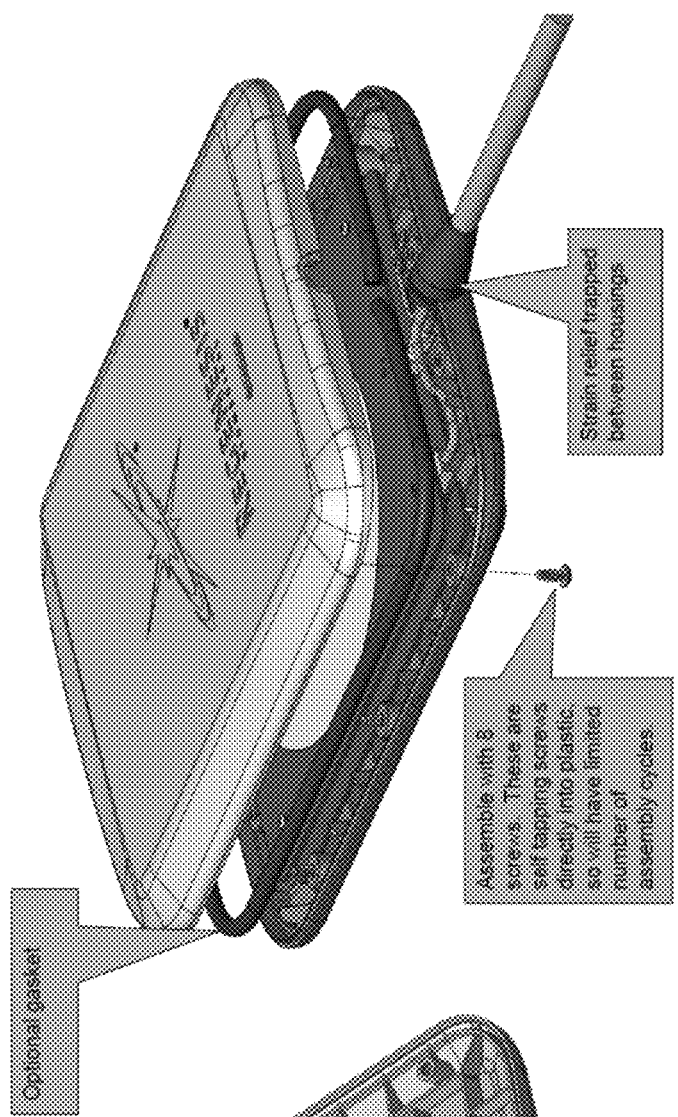
Figure 26D:
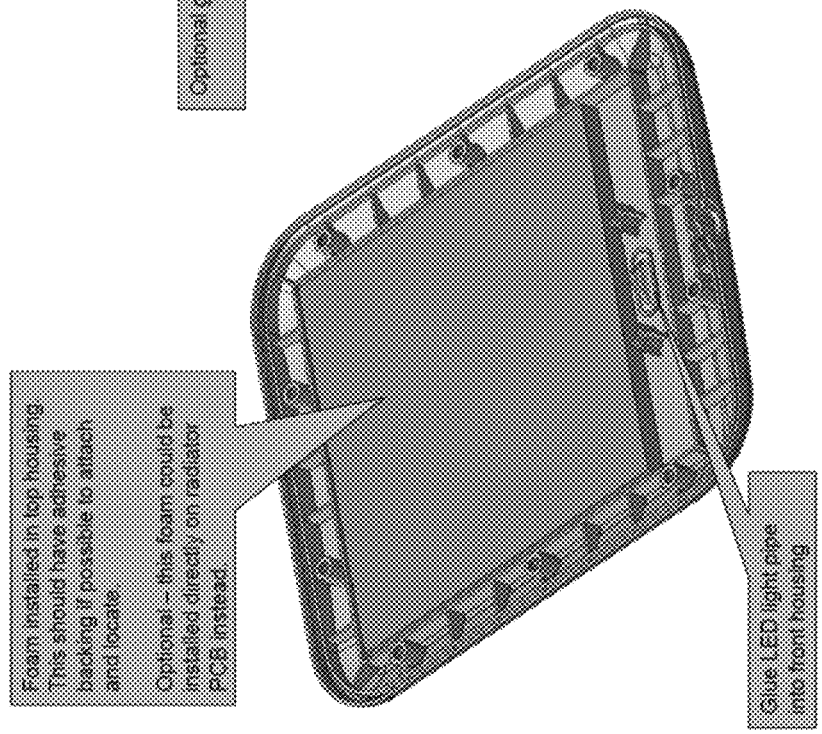

The internal PCB assembly for the RFID is illustrated in FIGS. 25A and 25B. In this example, the apparatus is shown with the RFID attachment shielded and opposite from the radiator PCB. An example of an assembly of an entire applicator is shown in FIGS. 26A-26E, showing the layered configuration of the applicator.

Figure 29B:
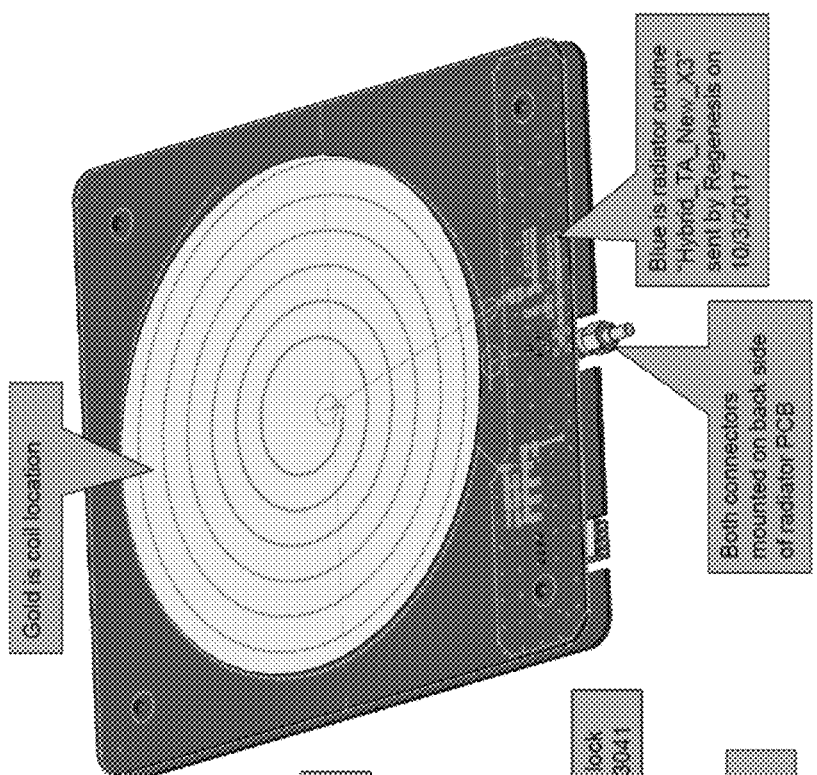
FIG. 29B is a schematic of a PCB showing the PEMF antenna (coil) portion.
Figure 29A:
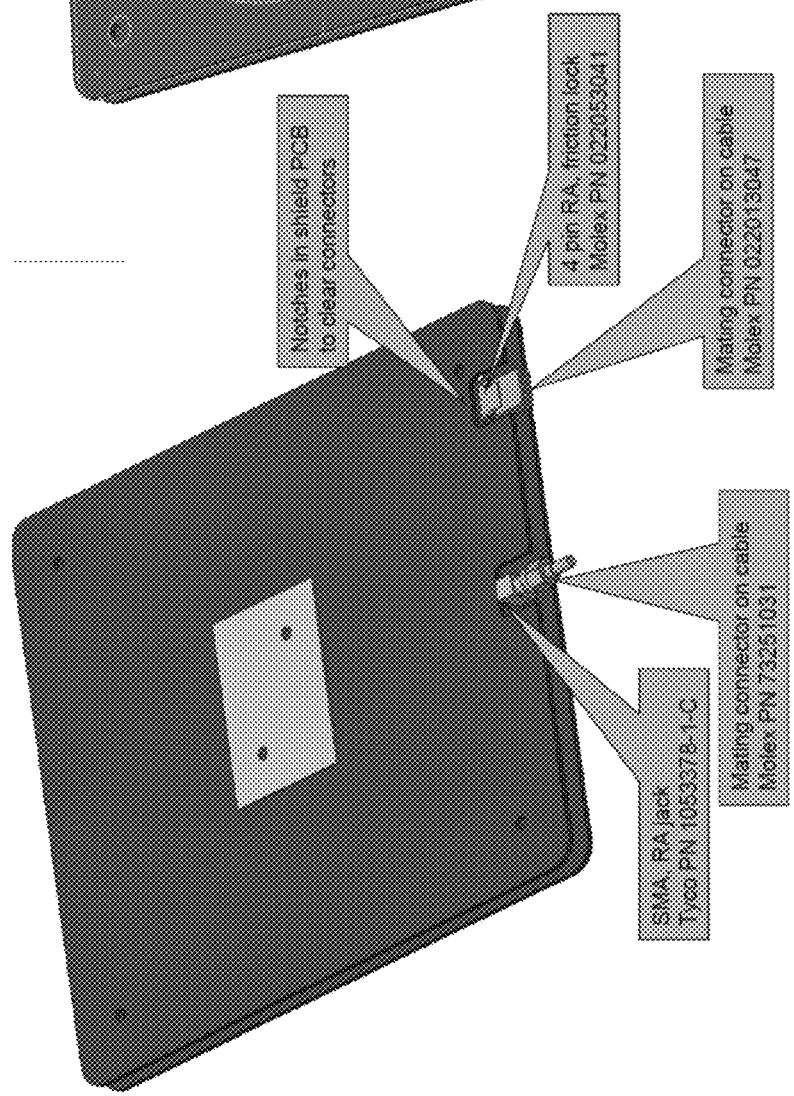
FIG. 29A is a schematic of a PCB holding an RFID opposite to a shielding region.

FIG. 29A illustrates an example of a shielding PCB, while FIG. 29B shows an example of a PCB with an antenna shown. In FIG. 29B, the antenna is configured similar to that shown in FIG. 8C. In general any of the applicators described herein can also include one or more tuning/matching circuits.

For example, for RF circuitry, a high power means a power of 40 W or higher. As shown the base housing can include a controller. The controller can include a processor, for example, an embedded microprocessor. The controller can include an FPGA block in addition to an energetics firmware. The base housing can further include a display. The base housing can have a user interaction interface and programmable functionalities.

For example, in some variations, the controller can have a cellular module, which can be configured to communicate with a server wirelessly and monitor compliance remotely. The controller can further include a memory unit to store data on the system. The controller can further comprise a diagnostic unit configured to run diagnosis and generate an error code. The diagnosis unit can be configured to run a diagnosis on the system when the system is powered up. The diagnostic info (and compliance/use info, etc.) can be displayed in the display. When the diagnosis unit detects a problem, the diagnosis unit can generate and display an error code. For example, the error code can be stored in the memory of the controller. For another example, when there is a cellular module, the system can make connection with the cellular network and upload the diagnostic info (and compliance/use info, etc.) from prior use. The diagnostic info can be sent to the server, along with a unique ID for the system.

For example, each of the one or more applicators can have a unique radio frequency identification (RFID) tag. For example, the controller can further comprise a radio frequency identification (RFID) reader. The radio frequency identification (RFID) can be transmitted through the one or more cables to an RFID Tune/Match circuit in the one or more applicators. The antenna is co-located with the RFID tag in the one or more applicators. When the user presses "start therapy" on the system, the radio frequency identification (RFID) reader may automatically (as an initial routine) read an RFID tag on each applicator; if the radio frequency identification (RFID) reader determines the RFID tag fails, the controller is configured to not proceed with the treatment. Indication of failure of RFID is displayed as well.

In some variations, the apparatus may be configured to operate sequentially. For example, apparatus may comprise two or more applicators. The one or more applicator further comprises an address decoder. A power control signal can be transmitted to the one or more applicator with an address, only the applicator that matches the address can be activated. In this way, the one or more applicators can be turned time sequentially.

The high-power pulsed electromagnetic field signal may have a carrier frequency of about 27 MHz. For example, each applicator of the one or more applicators can further comprise a tuning/matching circuit. The applicator can further include a shield to protect the lower power portion in the applicator from the high power electromagnetic field emission of the coils.

The applicator can further include a band pass, a first matching network and a second matching network. The matching networks are necessary for impedance match. For example, the first matching network can be configured to match network for 50 Ohm impedance. The second matching network can be configured for output matching from 50 Ohm to coil impedance free space.

In general, an applicator can include the shield to protect the lower power portion from the high power electromagnetic field emission. For example, the shield can include multiple shielded areas inside the four rectangle areas to protect the four segments of the circuitry: the RF drive, the band pass filter, the first and the second matching networks. Alternatively, a single shielded region may be included.

The applicators can comprise a feedback circuit positioned behind the coil circuit and configured to detect a field strength of the high-power pulsed electromagnetic field signal emitted by the coil circuit and send back the detected field strength to the controller in the base housing. For example, the controller is configured to adjust an amplitude of the high-power pulsed electromagnetic field in response to the detected field strength by adjusting the low-power control signal, thereby achieving a constant level of field strength. U.S. Pat. No. 6,334,069 discloses details of the feedback circuit.

In some variations, the feedback circuit is printed on a first side of a printed circuit board and the coil circuit is printed on an opposite side of the printed circuit board.

When the feedback circuit is printed on the same side of the coil circuit, the feedback circuity may capacitively couple to the coil circuit. For example, even though the field strength is decreasing, the measured field strength can be still high because of capacitive coupling, thus resulting inaccurate measurement. By printing the feedback circuit on the opposite side of the coil circuit, capacitive coupling may be eliminated.

In some variations, the applicator further comprises a shield board configured to shield one side of the coil circuit. The shield board only allows the electromagnetic field goes in one direction. The applicator can further include an antenna board for RFID tuning and matching.

When the signals pass through the coil circuit, the coil circuit generates the electromagnetic field. When the patient brings a body part to be treated in the range of the electromagnetic field, the body part becomes a part of the circuit, thus the electromagnetic field power being delivered to the body part to perform the treatment. The applicator may include a first network and a second matching network. For example, the first matching circuit may covert the amplifier impedance to 50 ohm impedance. The band pass filter may limit the carrier frequency to 27 MHz. The second matching circuit may match the impedance of the coil circuits. Without impedance matching, the power transfer is low-efficiency, which might result in overheating of the electronics. When the impedance matches, the power transfer is high-efficiency. It is advantageous to match impedance to maximize the power transfer.

Also described herein are methods for treating a patient with high-power pulsed electromagnetic fields.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A high-power pulsed electromagnetic field (PEMF) applicator system, the system comprising:
   a base housing comprising a controller configured to generate and multiplex a high-power pulsed signal, the base comprising a tuned switching power amplifier comprising a single-pole switching element configured to generate a pulsed drive signal, and a plurality of RF amplification stages; and
   two or more applicators coupled or configured to couple to one of the RF amplification stages of the plurality of RF amplification stages in the base housing, wherein each applicator comprises:
   a coil circuit configured to emit the high-power pulsed electromagnetic field signal,
   a feedback sensor configured to receive a feedback signal from the coil circuit, and to transmit the feedback signal to the RF amplification stage connected to the applicator, wherein the feedback signal modifies an operation of the RF amplification stage to increase or decrease an intensity of the emitted high-power pulsed electromagnetic field signal,
   wherein the two or more applicators are configured to apply the multiplexed signal to the two or more applicators so that each applicator emits a PEMF signal without interference.

2. The system of claim 1, wherein the high-power pulsed electromagnetic field signal has a power of greater than 40 W.

3. The system of claim 1, wherein the feedback sensor comprises a capacitively coupling feedback sensor.

4. The system of claim 1, wherein the feedback sensor comprises a capacitively coupling feedback sensor adjacent to the coil circuit and configured to sense an electric field (E-field) through capacitive coupling to the coil and the E-field reflected from a user.

5. The system of claim 1, wherein the feedback sensor is coupled to a digital filter configured to convert the sensed feedback signal to a digital signal for transmission to the RF amplification stage.

6. The system of claim 1, wherein the feedback sensor comprises an inductive sensor that is spaced from the coil circuit so as to avoid capacitive coupling to the coil circuit.

7. The system of claim 1, wherein the feedback sensor comprises an inductive sensor configured to detect a magnetic field (H-field) emitted by the coil circuit.

8. The system of claim 1, wherein the feedback sensor is configured to sense both capacitive and inductive feedback.

9. The system of claim 1, wherein the feedback sensor comprises an optical sensor on the applicator configured to indicate proximity of the user's body.

10. The system of claim 1, wherein the tuned switching power amplifier comprises a class E power amplifier.

11. The system of claim 1, wherein the tuned switching power amplifier is configured to generate a drive signal comprising a carrier frequency that is about 27.12 MHz and has a stimulation pulse width of between about 1 microsecond and about 200 microseconds.

12. The system of claim 1, wherein the tuned switching power amplifier is configured to generate a drive signal comprising a carrier frequency and a stimulation pulse width of between about 1 microsecond and about 200 microseconds at a pulse rate or between 0.5 kHz and 2 KHz.

13. A method of controlling operation of high-power pulsed electromagnetic field (PEMF) applicator system, the method comprising:
   emitting a high-power PEMF signal from an applicator of the high-power PEMF applicator system, wherein the high-power PEMF applicator system includes:
   a controller configured to generate a high-power pulsed signal,
   a power amplifier configured to generate a pulsed drive signal,
   a wireless communication circuit, and
   an RF amplification stage configured to couple to the applicator, wherein the applicator includes a coil circuit configured to emit the high-power pulsed electromagnetic field signal and a feedback sensor;
   receiving a feedback signal in the feedback sensor from the high-power PEMF signal emitted by the applicator;
   transmitting a therapy field feedback signal including the feedback signal received from the feedback sensor to a remote server; and
   transmitting, from the remote server, an alert to a user operating the high-power PEMF applicator system when the therapy field feedback signal exceeds a predetermined set of performance parameters.

14. The method of claim 13, wherein emitting the high-power PEMF signal comprises emitting a high-power PEMF signal having a power of greater than 40 W.

15. The method of claim 13, wherein emitting comprises emitting the high-power PEMF signal from a plurality of applicators coupled to the high-power PEMF applicator system.

16. The method of claim 13, further comprising adjusting the high-power PEMF signal emitted based on the feedback signal.

17. The method of claim 13, further comprising transmitting, from the remote server, a prescription for additional high-power PEMF signal.

18. The method of claim 13, wherein receiving the feedback signal comprises receiving one or more of: a capacitance signal and an inductance signal.

19. The method of claim 13, wherein receiving the feedback signal comprises a field strength signal indicating the strength of one or more of an applied electrical field or magnetic field.

20. The method of claim 13, wherein receiving the feedback signal comprises receiving a signal indicating contact with a body part.

21. The method of claim 13, wherein transmitting comprises transmitting via a cellular transmission from the high-power PEMF applicator system.

22. The method of claim 13, wherein transmitting the therapy field feedback signal comprises transmitting to a user wireless communications device and transmitting from the user wireless communications device to the remote server.

23. The method of claim 13, wherein transmitting the therapy field feedback signal comprises transmitting compliance data based on the feedback signal.

24. The method of claim 13, wherein transmitting the therapy field feedback signal comprises transmitting in real time.

25. The method of claim 13, wherein transmitting the therapy field feedback signal comprises transmitting at a start of a next session of the high-power PEMF applicator system.

26. The method of claim 13, wherein transmitting the therapy field feedback signal comprises transmitting at an end of a therapy session of the high-power PEMF applicator system.

27. The method of claim 13, further comprising confirming a transmission path before transmitting the therapy field feedback signal.

* * * * *